US012263205B2

(12) United States Patent
Rivella et al.

(10) Patent No.: US 12,263,205 B2
(45) Date of Patent: Apr. 1, 2025

(54) METHODS OF IMPROVING ANEMIAS BY COMBINING AGENTS

(71) Applicant: The Children's Hospital of Philadelphia, Philadelphia, PA (US)

(72) Inventors: Stefano Rivella, Philadelphia, PA (US); Carla Casu, Philadelphia, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 1009 days.

(21) Appl. No.: 17/049,050

(22) PCT Filed: Apr. 30, 2019

(86) PCT No.: PCT/US2019/029794

§ 371 (c)(1),
(2) Date: Oct. 20, 2020

(87) PCT Pub. No.: WO2019/213016

PCT Pub. Date: Nov. 7, 2019

(65) Prior Publication Data

US 2021/0252106 A1 Aug. 19, 2021

Related U.S. Application Data

(60) Provisional application No. 62/664,327, filed on Apr. 30, 2018.

(51) Int. Cl.

| | |
|---|---|
| ***A61K 38/18*** | (2006.01) |
| ***A61K 35/33*** | (2015.01) |
| ***A61K 38/17*** | (2006.01) |
| ***A61P 7/06*** | (2006.01) |
| ***C12N 15/113*** | (2010.01) |

(52) U.S. Cl.

CPC .......... *A61K 38/1816* (2013.01); *A61K 35/33* (2013.01); *A61K 38/1793* (2013.01); *A61P 7/06* (2018.01); *C12N 15/1138* (2013.01); *C12N 2310/11* (2013.01); *C12N 2310/341* (2013.01); *C12N 2310/351* (2013.01)

(58) Field of Classification Search

None

See application file for complete search history.

(56) References Cited

U.S. PATENT DOCUMENTS

| | | | |
|---|---|---|---|
| 8,076,306 B2 | 12/2011 | Monia et al. | |
| 8,173,601 B2 | 5/2012 | Knopf et al. | |
| 2005/0053587 A1 | 3/2005 | Galipeau et al. | |
| 2016/0046690 A1 | 2/2016 | Kumar et al. | |
| 2018/0105817 A1 | 4/2018 | Guo et al. | |
| 2021/0252106 A1* | 8/2021 | Rivella ................ | A61K 9/0019 |

FOREIGN PATENT DOCUMENTS

| | | |
|---|---|---|
| WO | 2010/065496 A1 | 6/2010 |
| WO | 2012/135246 A2 | 10/2012 |
| WO | 2013/070786 A1 | 5/2013 |
| WO | 2016/090077 A1 | 6/2016 |
| WO | 2016/161429 A1 | 10/2016 |
| WO | 2016/183280 A1 | 11/2016 |
| WO | 2017/068090 A1 | 4/2017 |
| WO | 2017/079745 A1 | 5/2017 |

OTHER PUBLICATIONS

Blum, et al., "Clinical Trial Showing EPO-Independence for 7 Months by Prolonged Secretion of Autologous EPO by TARGT" Molecular Therapy (2015) 23:S13.

Piga, A., "New Drugs for Modulation the Erythropoiesis in Hemoglobinopathies" Leukemia Research (2017) 61(S1): S5-S6.

Langdon, et al., "RAP-011, an activin receptor ligand trap, increases hemoglobin concentration in hepcidin transgenic mice" Am. J. Hematol. (2015) 90(1):8-14.

Wake, et al., "Generation and Characterisation of KY1066, a Fully Human Antibody Targeting the Enzymatic Activity of Matriptase-2 for the Treatment of Iron Overload in Beta Thalassemia" Blood (2019) 134 (Supp1):3532.

Schmidt, et al., "An RNAi therapeutic targeting Tmprss6 decreases iron overload in Hfe(-/-) mice and ameliorates anemia and iron overload in murine β-thalassemia intermedia" Blood (2013) 121(7):1200-8.

Guo, et al., "Reducing TMPRSS6 ameliorates hemochromatosis and β-thalassemia in mice" J. Clin. Invest. (2013) 123(4):1531-41.

Casu, et al., "Minihepcidin peptides as disease modifiers in mice affected by β-thalassemia and polycythemia vera" Blood (2016) 128(2):265-76.

Casu, et al., "Combination of Tmprss6-ASO and the iron chelator deferiprone improves erythropoiesis and reduces ron overload in a mouse model of beta-thalassemia intermedia" Haematologica (2016) 101(1):e8-e11.

Gardenghi, et al., "Hepcidin as a therapeutic tool to limit iron overload and improve anemia in β-thalassemic mice" J. Clin. Invest. (2010) 120(12):4466-77.

Gardenghi, et al., "Anemia, ineffective erythropoiesis, and hepcidin: interacting factors in abnormal iron metabolism eading to iron overload in β-thalassemia" Hematol. Oncol. Clin. North Am. (2010) 24(6):1089-107.

Soni, S., "Novel and innovative approaches for treatment of b-thalassemia" Pediatric Hematology Oncology J. (2017) 2:121-126.

Nai, et al., "Limiting hepatic Bmp-Smad signaling by matriptase-2 is required for erythropoietin-mediated hepcidin suppression in mice" Blood (2016) 127(19):2327-36.

(Continued)

*Primary Examiner* — Blaine Lankford

(74) *Attorney, Agent, or Firm* — Robert C. Netter, Jr.; Dann, Dorfman, Herrell & Skillman

(57) ABSTRACT

The present invention provides methods, agents, compounds, and compositions useful for administering to subjects having or at risk of having anemias. In certain embodiments, methods herein comprise administering two agents to a subject, which are useful for the treatment of an anemia.

26 Claims, 2 Drawing Sheets

Specification includes a Sequence Listing.

(56) References Cited

OTHER PUBLICATIONS

Wang, et al., “Reciprocal regulation between hepcidin and erythropoiesis and its therapeutic application in erythroid disorders” Experimental Hematology (2017) 52:24-31.
Casu, et al., “Hepcidin agonists as therapeutic tools” Blood (2018) 131(16):1790-1794.
Casu, et al., “Iron age: novel targets for iron overload” Hematology Am Soc Hematol Educ Program (2014) 2014 (1):216-21.
Oikonomidou, et al., “New strategies to target iron metabolism for the treatment of beta thalassemia” Ann NY Acad Sci (2016) 1368(1):162-8.
Casu, et al., “Correcting β-thalassemia by combined therapies that restrict iron and modulate erythropoietin activity” Blood (2020) 136(17):1968-1979.
Dussiot, et al., “An activin receptor IIA ligand trap corrects ineffective erythropoiesis in β-thalassemia” Nat Med (2014) 20(4):398-407.
Cappellini, et al., “A paradigm shift on beta-thalassaemia treatment: How will we manage this old disease with new therapies?” Blood Rev. (2018) 32(4):300-311.

* cited by examiner

SEQUENCE LISTING

```
<160> NUMBER OF SEQ ID NOS: 5

<210> SEQ ID NO 1
<211> LENGTH: 51000
<212> TYPE: DNA
<213> ORGANISM: Homo sapiens

<400> SEQUENCE: 1

tccttttctc tttcttttca agacagggtc ttgctctgtc acccaggctg gagtgcagca      60

gcacagttat ggctcactac agcctccaac tccagggctc aagtgatcct cccacctcag     120

cctccctagt agtgggatct gcaggtgtgc accactatgc ccagctaatt aaaaaaaatt     180

ttttttgta caaacagggt ctcactatgt tgactaggct ggtctcaaac tcctgggctg      240

aagggatcct ccctccttgg cgtcccaaag tgctgggatt acaggtgtgg gggtaagcca     300

ctgcacccag ccacgtctgt gctttcaaac acctctctca gcattttgct gctgcttgct     360

tattgccagc ccctcccccc aggccatgtc ggatcgatgg ccaggtggcc gccaggtcta     420

gaggacgtcg attgtgcaag atcggctttt cagactgtcg ggctagcagc ctgggctggg     480

ggcctgggcc ttttgacctt ccaaaggaca ggatggggta cagaggctag gatcggggtg     540

tcttcacccc ctacacaaac acactatccc tgctctgtct caagcatctg tccctcagga     600
```

```
agtttgcaag gtggggccca gggcctggga agaggggagt ttatggggag gaggcagagt    660
tgttggggct gggacgaggg acagtgggca gggctatggt gttcggtctc agggtcaggg    720
tcaggcccat gggcaggggc caggactctg ggagggccca caggagaagg tgagggaagg    780
taccccctaa cccagaatcc taaccagcct gacagtgcgc cctcctgccc tggcccagcc    840
ctggctctgc ctggagatgg tgctgtactg agctcatgcc cagcccccat gggcaggggc    900
cttcacacct taggacacag ggtgccccc cacgcacatg tcagggaggt acctgcctac    960
tgctacaggc ccccttaggg agcacacgcc agagagcatg gggcatctac gtgcttgaga   1020
catgcgtgag ggccacacag ggtaggcacc acacacatgc cacctgtcat tgcctggact   1080
tcagtgcaca ggcacacctg gccccgacac accagcgtgt caccatgaga agaggagaaa   1140
cccgctctcg gcgcccccca cagtgctggg ccttcgcaca cgttgtttcc cgttcatcaa   1200
gaaggggcga attttttca ttcgacagat ggaagaagca ccgctcagaa gtcagggaat    1260
ctgcccaggt tcctacaact aaaagggagc caggtagggc tgaaaaccgg cggtcacggc   1320
aaagcccggg cgcggggccc tgtcccatcc cagccaatcc ataagcatct cacacttcac   1380
acccgctgca cactccactc acacgcctca cactccacac atgcctcacg ctccacacac   1440
acctcacact ccacacacgt ctcacactac acacacgctt cacactccac acatgcttca   1500
cactacatac accttacact acacacacac ctcacactat gcacacacct cacactaaac   1560
acatgcctca tattccacac atactgtgag catgcacaca cacacacaca cagctgcaca   1620
cacctctcat gctccataca cacctcacac catacgtacc tcaaagacac acacacctta   1680
cactgcacat tcccagcacc cacactgcac acacatgcac agtccatatg cccacacaac   1740
acacttcaca caccccccac cccacaccat acaaacctca cagacacacc tctcacacaa   1800
atcttatacc ccacacacaa tccctacgct ccacacacac acacacacac acacacgcac   1860
attctacaca tacataatct acacacacaa attccagact gtctctctta cacacacact   1920
ctgggaccca tatgcccaca gcacacagca tctcaggcgt gcaccccgca ttctggcctc   1980
aggatgtaga ctcgctgaaa gtcagccttg tctgagacag acgcccgctg ccctgcacgc   2040
accctagaaa gccctggctc ccatccggca cttcggcacg catatggctc aaacccatct   2100
ccacagcaac gctgttccat agaacaacaa cgcaggtcac acttgtgact taacctgtct   2160
aatatccaca tgcaacaagg ggtgtggtgg cccgcgcctg taatcccagc tacttgggag   2220
gctgaagcag gaggatcatg tgggcccagg agctccagac cagcctggca acctaatgag   2280
accctgtctc tgaaaaaaaa aaaaacaaga gagccagaag aaaattgctt ttaataatac   2340
attttattta tcccatgatc accagtgtta tttcaacata aaatcaatat aaaaattgtt   2400
atcgcgttgg ttgacatcct gtttgcactt ggccttggaa acctggtgtg cgtctccccc   2460
gtgcagcttt tctcagttca gactgactca agagccacgg gtgaccagcg gctaccgtca   2520
tggacagcac agcgctacgg aaccaggtag gaattcatgc tgcgtgcggt cgctcatgcc   2580
tgtaatccta gcgttttggg aggtcgaggt gggtggaatc acttgaggtc aggagttcga   2640
gaccagcctg gctaacatgg tgaaacccca tctcttctaa aattatgaaa attagccggg   2700
catggtggtg ggcgctgtaa tcccagctac ctgggaggct gaggcaggag aattgcttga   2760
acccgggagg cggaggttgc agtgagccga aatcacacca ctgcactcta gcctgggtga   2820
cggagtgaga ctccatctta aaaaaaaaaa aaaaaaaaaa aaagaacgag gtaggaattc   2880
aaataattcc cagctaaaca gaaaatagca tcaaacccca cccctgcctc ccctttctcc   2940
```

-continued

```
tctccagtcc ccagagtata tgggcccagc ctccttttct ctctctcagg ccagcagctc   3000
ctttagtctc gcctgtccag gtaagcacct ggactcaccc ttgtgagccc ctgcactcac   3060
ctgcaccggc ctctgcacag tccccagtcc ttggctgtcc ctacctcatg ctctcgggga   3120
ccaggggctg taaccaggca ggcatgtcac caggcaacgg gcctcggggg agagctcaga   3180
tctcccgcac ctgcctgcca gcctctgggg tgcccatgcg ggggtggggg aagatggggc   3240
ggggcaggca ctgccttctc ctacctcctg cctgtttacc tgtacttagt cacagtgctg   3300
tccaggaccc agcaggagga gttccatgga gcctgaggcc acaggccaca ggggacaagg   3360
gccagacacc ctggtcatgg ctctaggcca ttgatccagc ctgggctggc tgggtggggg   3420
tggggaggcc ttggcctgga caaacagagg ctcctgaggc ctgtgtgcag gcccggcacc   3480
tatctgccgc tcccaaaggt aagcgggggc ctccaggaca ggggaccggg atctataaat   3540
gacctagtga cagtgtccac cctaagagct gggcctggct ccctgcagcc tgagccacct   3600
accctgctcc gaggccaggc ctgcagggcc tcatcggcca gagggtgatc agtgagcaga   3660
aggtgagggg cccacagagc tggggagggg agggaccacg cagggtgaca ccaggtgtgt   3720
ggacaggcac agcatcagtg ctgggtggtt ggtggcctgg gattcaggtg gcagggacag   3780
gaggaaggga gaggccaccc taccccctgcc tcgcaggact ggacatgctg ccccctccac   3840
acccggtacc ccacctgggc cttctggtgt aggagacagg cccggagccc cacattgcac   3900
ctatgtactg acttaagccc aggaccctgg gctcacaggc tcagagttgg catgtatgtg   3960
tatgtgtgtt cgtgtgtgtg tctgtgtagg aagggcgtgc atctatgaat ttttgtgtca   4020
tgaatagatg tgcgtatatc cctccgcgtg tctccatctg tgtacatctg tgggtctgtg   4080
agtgtgttta tatgtgtgga agggaccccc acccagtccc ccacactctc aggactctag   4140
ggcctaatgg tttcactgaa agatgcccct atggccctag cccagagtcc ctgctctgct   4200
ctgctctgcc ctggctgagg gacctcgggt aagtcatgtt acctctctct acctcagttt   4260
ccccagccat taaatagagt cagcaaagta ggcaccccag gctgttggag gctgcagtgg   4320
agtttgcagc actgcccagc acagggctgg cacatggtag gagttcatac gcagtggttg   4380
aatccggatc tgcattgctg ggggagtcgc ggccccgccc caaggagctc agcctccagc   4440
aggcagaccc gagaccctcc aatggccaga agggcaggag ggagtgagga gcaggtgcca   4500
gggtggggtc catggtgctc agagctgggg gactgcttca ggcccctgtg gcaattggag   4560
cacagtcccc gcttccagga gttcaatgtg aggggcaaag agagagtgcc cacaggtaag   4620
ctgcacatcg cgaggggcag ccgccccttc tagggcactc tgggagagct gcgaagaggt   4680
gaggtctgaa ctgaggtgac aggggctgca taagagctgg ccaggttggg aggtgggggc   4740
ccaggcagaa ggaagagtgt ggggacgcct ggccgtgaac aagcactgac agggctcaag   4800
gtccacgagg gctcttggtg ccggctggct gctcttaatc cataaatgtt tgctaccatc   4860
ccattgttaa aatttctcac caatggaagt ccagtgtcct tggggtgcga cggggaaaag   4920
agagggtggg aaaaaaggag gcaggagaag ttggccaggc cacatatgca cacagcacct   4980
tggacttctg tagggaggaa ggagctggga ccttgtcatt cattcattta acaattactg   5040
agtgtccgct gagtaccaga ctctgctctc atgcagctta cagacaggga ggaggcagat   5100
aaatgacata tttgcatatc aggcaattta ggcctctgta attgctataa agaaaaatgc   5160
aggagagacg ggagtgccca gggaaggcct ctctggagag gtgacatctg accctttgga   5220
ggaggtaaag gagggagcca cgaggccagc agaaaggaaa acatcccagg cccagcaagg   5280
agcaaacctc ccattcagca aagaggacag gaaaactgag accctgggtc tttagggact   5340
```

```
gtgttctagg tggatggaag ccgtgcgagg cttgtgggca gggcacatgg tgacaacacg   5400

cagtggccat tgtgtgagaa ctcactgggt agggggggtgg gtgattggct attgcaggag   5460

tcgaggtgac agatgacggt ggcctggatg atggtgggag tcatgggggg ccaagaaggg   5520

gctggctttg gggggcattt ggaaggtagg gccacaggct tttccaaagg tgctggaccc   5580

tgggaatggg ggagccgttg tattataaga tagtaaagac aagagtggca ccgtcatctt   5640

cacaactgtc cactgcccct cctcctgctg ggcaggaaac ccaagaggat gggaatgagg   5700

tctcttagag tcaccatgtg ccaccctgtc gccaccacag agcctggcac caagcaggtg   5760

ctagacaaag atagggtgac tgagcattga acctgggacc ccacaggccc acaccattgt   5820

ccatgcccca gtgccaggcc tcacaagtcc tccttcctgg aggcagcaag atagaaagcc   5880

ctgtaccagg ggcctagaga cttggcagtt tcattcactc attctttctg atccttcact   5940

catgtgacgg gctgtgcggc gttccatggg gaaccccaga ggtgagcaag atgctggccc   6000

tgcctgttct gtaggggaca gaggcaagac ccaaagccaa ggcatattct tgatctgatc   6060

aagggctgcc caggggaggg ggcagcttaa ctagccaggg gcccagaacc cagtgcctgg   6120

caggtcgcct ggtaagagtt ccccacagtc caggcagggg gactcagctg cacaaaggca   6180

gggtctcgtg ggcctggggc accatgtgca tgatggaagt tatagccacg aggagggtgg   6240

acagcagcct ggccatggag ggtcttggat gtcgcagcaa ggggtttgga tgataagtgg   6300

ctgggagctg tgaaaggatc ctgagcaggt gagcgattga gctggggagg gaggatgcgc   6360

tggaagacgc aatggaggca ggggacctag tgaggaggcc gccccagggg tttgggtggg   6420

aagttatgat gagcccgggg gaattaattt cccactactg ccatttggac catggcttgg   6480

gtttttacag agggtgtcct gaaaatgagc ctctctgtgc tgctcaaagt cctcccagat   6540

ggatgcgagg ggcatttaga gggaggcaaa atctgcatag agaaggacgc ctggcttgga   6600

ggatgagagg ggaggggagg cccaccaagc accccaccat gagctgcccc tcttcgggct   6660

tcctctaatg gacccacgac ctgctccgag cctcagtttc cctctcttta cactgattat   6720

ctgagaggta gtagggctca gtgatcaggg cgtcactctg aagtcaatct gcttgacttt   6780

gcagcctggc tgtgctgctg accagctgtg tgaccttagc caagctgctc aacctctctg   6840

tgccttgact ctcccatctg taaagtagga gtgatcagag tacctgtccc cacaggatct   6900

gtgtaaggct tacatgagaa agtgcacata aagcaacaga gacaattgaa ataaatgtca   6960

cctgttacca cctctatgcc cccgagtccc catggctcta tgactcatcc caaaatagct   7020

cctttgtgat ccagactcaa gagtaaaaca gggccaggta tggtggctca catctgtaat   7080

ctcaacactt caggaggcca aggtgagggg atcgcttgag gccaggtgtt tgagacctgg   7140

tctctacaaa aaataaaact ataaaattag ccaggtgtgc tggtgcacct gtagtcccag   7200

ctacttggga ggctgaggtg ggaggatcac tcgaacccag gagttggagg ctggggtgag   7260

ctatgatcgt gctaccatac tccagcctgg gtgacagagt gagatcctgt cccttaaaca   7320

aaaggggtgc gacgggaata tggtgtcctc ctctggcaga gggaggggac gagggactga   7380

aagaagggca aggagccaac ccatcacctg ggatcttccc aatccagcaa accttctcag   7440

attttgagga cagccacctc agtcagaggt ggccagccca ggacagacag gcagctctgc   7500

gctggggact caaacctgcc atgtggcctc atgcaagagt ctcagcaccc tgttactggt   7560

ctgtttcttg cctgtttctc actagggatg ctgtgaacat ttgaggaagt gggcggggct   7620

gtcccacccg ttgccggacg tttaccattt accattccct ggccttggcc ccataaaagc   7680
```

-continued

```
cagtagggcc cactccacat gcaggaatgt cctagcttag ttgtggaggg ggatgtcatg   7740
cccagtgagg gtcccctgca gtccctccct tccttgtatc tgatgggggc cgctcaacag   7800
agtcactgtg gcttgacacc aaagaccctt agctgggaac gatgccaagg ggagctggag   7860
ggagccagga agctgggaga agggccaggg cccttcacat ccacctggga ggactttgag   7920
cattactaaa gagccccgtt tttggaaacc cgctgtgtaa aatcccaaga tacagcccaa   7980
aggaagcccc gcctgcatct ggggtgcatt ttatttattt ttttatgttt ttttttttct   8040
caagcagagt cttgctctgt cacccaggct ggagtacaat ggcatgatct cagctcactg   8100
caacctcccc tgaccaggtt caagtgattc tcctgcctca gcctcccgag tagctgggat   8160
tacaggtgcc caccaccaca gccggctaat ttttgtattt ttcatagtga cagggtttca   8220
ccatattggc caggctgatc tcgaactcct gacctcaggt gatccactca cctcagcctc   8280
ccaaagtgtt gggattacag gcgtgagcca cggcacccgg ccctggggtg cattttaaag   8340
ctacacggta tttatggata tagtaagagg agatgaactt cgcagtagtc tggagccttt   8400
gctctcccgg tgggtgggtc aaaggctttc tctgtactgt ggggaaacct gcgtcaaagg   8460
ccaaatacat tgggatgttt gcttgaaagg gtctcaaaat agagttggaa ccctggagcg   8520
tggagagggg cgacattcag ttgctattta atcatgattt gttaattaac agctcattta   8580
tgggaggcat cttagattcg tggaaaaagc agggagtcag acatctagac tcaacctcca   8640
cttccctgct gtgtgatctt gggcaagcgg cttagcctct ctgggcttca gggttttttt   8700
aatctgtaaa atgcgtctgg gagtgaatgt caggtattca aatcacactg ggaaaatggg   8760
gctaggaaaa gccctagact gagttagtgc tagaacactc tgggtctcag tttccttatc   8820
tgttcaatgg gtgcagaact ggaggtttaa gtgagataaa gcaggtgaag tacccacgtg   8880
gtgtgggctg gaggaagaaa acatgggaca atggttccac atccctgggt gacctgaaaa   8940
ttaagtgtga gatgtctcat gagggcacga aatgaatatt agtttttgtt cccttcctct   9000
gccacaagac tttgagagca gaaaggtgag agagacggta ctctgtgaag gaaggcaggt   9060
ccccggccca gcgcagtgcc agctcagggg attctggggc gggggctaag tgcatggact   9120
gtgtgggcgt ggtgggaagc tccgtgaacc agaaccagga gcaagaaaca gcattccttg   9180
cgtggacggg aaatgagggc aagaggtcag atgtctacag aagtctgcac cccatgtact   9240
tcagttctgt ctgtgggtgc agcctctagg gaggtgggtg tttaggtact gagacctccg   9300
tctgtcctct gaccataggg aagccagtgg gaagcaaagg tggggttctt gagccagacc   9360
cagtccagct ctggtgcctg ccctctggtg cgagctgacc tgagatgcac ttccctcctc   9420
tgtgagctgt ctcggcaccc acttgcagtc actgccgcct gatgttgtta ctcttccact   9480
ccaaaaggca gggaagtcct gcttccgtgc ccccaccggtg ctcagcagag gctcccttgc   9540
aaatgcgagg ctgtttccaa ctttggtctg tttccctggc aggatgcccg tggccgaggc   9600
cccccaggtg gctggcgggc agggggacgg aggtgatggc gaggaagcgg agccggaggg   9660
gatgttcaag gcctgtgagg actccaagag aaaagcccgg ggctacctcc gcctggtgcc   9720
cctgtttgtg ctgctggccc tgctcgtgct ggcttcggcg ggggtgctac tctggtattt   9780
cctaggtaac gttgtgggac cgcctgggag aggcacctgg ggaggacttg gggtgactgt   9840
agcaggcaca gcaggacagg actgggttcc aggctcagcc gtgcttagca tattgctgtg   9900
tgaccttggg caagtcactt ctgttctctg ggtctccctc cctgtccttc cagctggaga   9960
tgctgtcaga ccctggctcc aggtcctatg gctcgggtct gcttcctgct tgggcaaagt  10020
gccccaaagc tccccaccag gtggggaaag tgggccctcc tagcacccag ttcttgtgag  10080
```

```
ccagccagcc cacagagcat aaacatcgcc ttcccttgcc tgcagtcctc ctgggttgcc  10140
cctgaggctt ggagccaacc cagccctaaa gaaggaggcc cagaggcacc aatggtacct  10200
ggtaccaatt agtgcctctg ctcacttgag cctagcctag gttctcctct aggctgggga  10260
ccacagctct atcccctctg ggtctccagg gtccagcatg aatgggggac ggagcaggca  10320
gctggagagc agccagcctt ggggccctct gccatgtcct taattatggc tggcccctcc  10380
ctgatgtcac agccctcagt cagtcccctg gtgcccgggg agcaattggc ctgtgctctg  10440
ggcccattca tccaggcctc cgttcattca ttcatggaat aaatgctctt gagcatctat  10500
tatctttctc taagattgat ggagtctctc ctcttccttc tgcctttgac agtgggaagt  10560
aatggagaaa ccaaatcgga ctgtgcctct acactgtaca ctgtagaagg cccattcatt  10620
tgttcattta ctcagtgcca agcacctcct gtgtgccagg ttctggggat agcccctgtc  10680
cttgtgattt agccaaggca tcagacctga catttacgct aaagcatagc atgtgatggg  10740
acagaggaag ctgagggctg ggaagccaca ggagggacaa cccagatgcc tgcgtgatca  10800
gaagcatccc attaaacatc ctgcaaagga tagctagtgc tcttactggc tgaatctcct  10860
ggtggaattc caggcctgtt gaaagcaacc tggggaccaa ctttgtagca gtggagagaa  10920
atccatgtag gcctagatcc aaggggtcag ggttgggagt gtctggaacc agcatctggg  10980
agtgacacta ttgggaaccc caggtctgac acgggcctgc ttgcaatgac ttatagtgat  11040
tctacccaga gttgagcaac gcaggcagta gacgccatgt gcatttcacc accagcagga  11100
agccagtgcc ccagatagca cagggctgtg gggcctcct caggtagcgg gctaattagt  11160
ctacagggta aaccacgggg cactgggctg gagggccagg aactcacctg ccaattattt  11220
ctctttgcag aggagtttaa ttccccctga ttatgctcct ggggtaaatc accccccacc  11280
ccaggagagg tgctccatgg ggctgaggac ccaaggggtg agtgctccca agcctctgct  11340
gggggaagcc aactccccca cagagggatt aagggttgaa ggaggcactt tgggagctgt  11400
ttgaaagact cctcccgcct tgaccaggct gtgctcctgg gactgggcgc tgggcaagga  11460
agtggatcag agacacgccc tgccctgtct ggaagaggag gtgcacaagt gaccagtgac  11520
actggagcag gacaggcccc aagcgaggag gacagcctgg cccgaggaga gggtgtggct  11580
ggcttcctaa ggatggtagc aggaccctta ataccaccaa ccatatttcc tgggtccttt  11640
ccctttcctg ctctcccagg caagagtttt atgtgttctc aagcccccag cacccgcctg  11700
cccctgtctc ctgcttcagt gagaaaacaa aacagcttag aagagaagcc ccatatatgt  11760
tggcccacct gccctcccag ctgcatcacg tgcactcctc ctgggacccc gatcccgccc  11820
cctctgccca cacaatggcc cagcaccagc aaggatgccc tctctccccc agtgtccctt  11880
ggggtgcctc ccccatttct ctgctccttg aaagagctgt cagtccacac acccagtctc  11940
tctgtgccct ttccaacctg gctccctctg ccccccaact ccaatggcca ttgtcaagct  12000
cgccaacatc ccaggttgct aaatccaatg tccacttctc agtcatcatt gcacttgacc  12060
cgggggctca cccccacctc cagaagccct ttcctcccta gactttgggc cgccaccggg  12120
tcctttccgc tcagcaggtt gctttttctg tgtccctgct gatgggtggg gcctctcctt  12180
tctctctcca cccgcttctt tcgtgatctc atctgctacc cttagcttca agtgcccttt  12240
ataccctgat aacacccaca tttgcatttc tagcctgggc ctctcccttg agcttgtctc  12300
tagagctgcc cctgctcttc ctcttaatgt ctaaggagca tctcggaccc tatgctttca  12360
gaccatgagg tctctgcata atttccccca gacctgtacc tccaacatcc cagtccaaga  12420
```

```
ccacttcttt ctggcacctt ccccttactc ctttctttct tttccaccca gccccacttt  12480
gccagcaaac ctggtcatct ctaactccaa aacacatcaa aagcagctga cgccaatcac  12540
ttcccaccct ctcctctgcc acagctgggg ccaggctctg tccccctgga catctctccc  12600
ctggagccct gcaggcgtgt cctcgatgct ctccctgcct ctgccctgcc tccttagagc  12660
ctttctcaac agcagaggga ccatttgata aagcaaacga aatcctctaa cttcgctgct  12720
taaaacctcg cttggggcca ggcgcgtggc tcacgcccgt aatcccagca ctttgggagg  12780
ccgaggcaga tggatcacct gaggtcagga gttcgagacc agcctgacca atatgcagaa  12840
accctgtctc tactaaaaat acaaaattaa ccgggcgtgg tggtgcatgc ctgtaatccc  12900
agctacttgc gaggctgagg caggagaatc gcttgaaccc gggaggcaga ggttgtggtg  12960
agcggagatt gagccattgc actccaagct aggcaacaag agcgaaactc tgtctcaaaa  13020
acaaaacaaa acaaaaacaa aaagaaaaca aaaaaaccac ctcccattcc tcccatctta  13080
cccagggtga aagcccgagt cctcccaggc ctggaaagcc ctacccagcc tctccccttc  13140
cccatctcat accctcctgc tgtcctgttg ctcactcttt gctgctcctg aaacacacca  13200
ggcctttgca cttgcccctg cctgggacat tctttccaca gatgtacatc accttcttcc  13260
ctgacctcca tatcgcagcc cgtcccatgc cctgattccc accgcactga ccacctctaa  13320
cctgttatac acgatgtgtg gtttaccgtc tgattccttg ctagtctaca agctattaag  13380
ggcagttttt tcttgatagt tctgtccgtt gttttgctca tatagtccca agtactttgg  13440
ctcagttcct acacatagca ggctctcaag aggtatttac tgagtaaatg gataggggtg  13500
taaaccaggg ctgtgagtct accctcttca cttcagccaa aatagccttt gcaaaacaga  13560
agtctgatga catcattcct gattttaaac ttttcatggt tacccttgtt catcgggtaa  13620
agacccaatg ggccctgccc tgcggaggcc ccagctcctt gccgcccctc cccatctctg  13680
actgctccag ccaaacaggc tttcagcccg ggtcctcacc atggtccccg tgctaccggc  13740
cccgtgcccc atgctgctcc ctctgctgga aggtacttcc ctccctcttc tcttaccaat  13800
ttacagtttc cccatcccta catctcagct ggagggtcac tccactctgg cccaggctga  13860
gtgtcctcgt cacatcccct caacagcacc atgtggcact gctccctgat ggcactgccc  13920
acagacagat gccacatgct gtgtggttgc cagagccacg cctttcttac ccaccactgt  13980
cagcttcaca aggggaggca catctgtctt ggttaactgg cgtaccccat gtagtaggtg  14040
gttagcacac actgtgggat ccctgggtga cctcacgagt ggaaggatgc ctagtggtgc  14100
tgacccatga ccttggcctc ctgggcctat gtggatttcc tggccttcat gtcattggtg  14160
tcctggactg gtcactgtgt cagcctctcc ctgggaacct gtaggacacc atccatctgg  14220
gagcctttca cctccctggt accttgcagc cagtttgtca tccaataaac tttagatgac  14280
catgatgaca atgggagtga caaagatgat gatgatgaca ttgatggtgc catggagacc  14340
caagacactg aggctgagct gagggtgtgg gtggcaggag aaggcatgga agagacagga  14400
gactttccca cctgcttcct ccactaaccc tgctggttcc ttcctgggca gggtacaagg  14460
cggaggtgat ggtcagccag gtgtactcag gcagtctgcg tgtactcaat cgccacttct  14520
cccaggatct tacccgccgg gaatctagtg ccttccgcag tgaaaccgcc aaagcccaga  14580
agatggtagg aaaggatctg gggatgaga gggagggaat atgggggtga aaagagaggg  14640
gtggggtctg atcacatgga gccagttggt caacccatct ggagcattca cagggaccac  14700
agccctgctc caggcaccat ggaagcagat gaggttgagg gtcatgggaa agttagtgga  14760
tgtttgggtc aatagcactc ggattagatc ctgatcatgc ctcttaccag ggtggagca  14820
```

```
tgaccttggg aaaggtccca cagtgcagct gacactattg agggcccgct cctgcccctc  14880
cgttacagga cggtggcccg ctcctccccc tccgttacag gacggtggcc cgctcctccc  14940
cctccgttac aggacggtgg ccgctcctgc ccctccgtta caggacggtg gccgctcctg  15000
cccctccgtt acaggacggt ggcccgctcc tccccctccg ttacaggacg gtggccctct  15060
cctcccccctc cgttacagga cggtggccct ctcctccccc tccgtaacag gacggtggcc  15120
ctctcctccc cctccgttac aggacggtgg cccgctcttc cccctccgtt acaggacggt  15180
ggccgctcct gcccctccgt tacaggacgg tggcccactc ctgcccctcc gttacaggac  15240
agtggccgct cctgcccctc cgttacagga cggtggcccg ctcctgcccc tctgttacaa  15300
gacggtggcc cgctcctgcc cctccgttac aggacggtgg ccactcctgc ccctctgtta  15360
caggatggtg gctcactgca cggaggctgg tctactgcct gccactctca ggctgcagga  15420
ccactgccca gcaaggcagg ccagaagtgc cggggagtta ttcccaggag caaccctgaa  15480
ccatgagcgc tggagtgggt ggatcaatac cgcagcttct ttggccctgg caggggggaat  15540
agttcacaga atgttccagg ctgtctccca gagatgccct attcggctga gctcagatgc  15600
tctcagctct acactgcgca ttcatggccc tgtgttggtt gcccactttc cagtctctcc  15660
ctcccaacta ctgtttccca gaatcacctc caaataaacc acttgcccca ccttgtcaat  15720
ggagggtctg cttctgaggg acccagcctg aggctgcccg tttcctcctc catgaggtag  15780
gggtgataac aacaggaccc ggctgcagat ttgttgtggg ttgcagtgaa gttgagataa  15840
cacgaacact attcccacgc tgcgcaaatg cttaagagcc tgtaatcctg ccagcagcgc  15900
tgtagttgga gatgcgcaaa aactacccat cagagctgct ggcttgtccc aggccatggg  15960
aggaggtgca gaggggaccc aggagccgag tggggtttct cagagttgag gagtgacttt  16020
tggcaagggg cagaggggtc atcagcagtg caggtggagg tgagagtcgg gtgtagtgga  16080
aacagaaaga aggggatggg gtgtgagatt catgcatgcc ccggcccggc cactcagcac  16140
tgtgtgaccg tgatcaagcc tgtccacctt ggagaatcat gcatggagcg gggctgccag  16200
taggagcaaa gggcacctcc aggtaggaag tgggcctgtc tgccctgcag agggtcccag  16260
gggctgttgt cttcccttct cacagctcaa ggagctcatc accagcaccc gcctgggaac  16320
ttactacaac tccagctccg tctattcctt tgggtgagtt gtccttgccc ctgaccagct  16380
cctgcaagaa gctgagattc aaagaatggg aggggcctct gtaggcttct gatgcaatgc  16440
cttcatgttt caaatgggga aactaaggca tagagaggga acttggcttc ctgcatgtca  16500
ccctcccttc actgggctca tctgtagaat ggaaacatgg gtgtgatagg tttgcaccag  16560
acaatgactg tgatggctga tcaagggcct gacaccatca ggcgaggcga tgttggaggg  16620
gcatggggtt aaaagcattg gctccagggc ccgactgccc cgtccacatc tggttctgct  16680
acttgcggca tagtttatga gacacaagtt cacctctcat gcctcagttt tctcattcgt  16740
aaaataagga ttatgagagc gcctccttca gaggtcgcta ggaggcttct gcgtgaagac  16800
ggacagcaat ggctgaggtg cggaaagtgc tcgatgtgca tgagcagggg tggagctggg  16860
gccagacctc agaatccttc cctggcctct ctcacttctg cctgccttag ggagggaccc  16920
ctcacctgct tcttctggtt cattctccaa atccccgagc accgccggct gatgctgagc  16980
cccgaggtgg tgcaggcact gctggtggag gagctgctgt ccacagtcaa cagctcggct  17040
gccgtcccct acagggccga gtacgaagtg gaccccgagg gcctagtgat cctgggtcag  17100
tactgcgagt ggaaacgtgg ggttggcctc atgaggttgg gggaaacaag ctgtggtgtg  17160
```

-continued

```
gcccggggag gctgcctgcc aggcctgggg tgctgtcagg gtgggccccc caggagagcc  17220
ccccaggtga ggtagcagtg ccattgcatt caaggagcca ggaaagaagg gtgggatggg  17280
ggcatttagg gtaaatctca gacaaggctg gctccaaggg tctcctctaa ttttattttc  17340
attgtatttt cttttctttt tttttttttt tgttcttgtt tatttgtttg ttcatttcct  17400
tttatcagaa gccagtgtga aagacatagc tgcattgaat tccacgctgg gtacgctatt  17460
ttttttttccc ctccccattt tccttttgag ttggcatttg tcttgacttt gttgtgtatc  17520
agggggacac atggcttctg ttgtgtgtgc agggagccct ggccaagagt cacccagggg  17580
atgccatggt ggactcagcg atgtgtccca agcaagtctt ggagcctgta gggggagagg  17640
aggtggcgac gtgcatgcgt gtatttgtgt gtgtcttgta gacgggtgtg catgcgttcc  17700
tgtgtgggtg tgaggatgag tcaggtttag tggtccacga acgtgactct cctctatcat  17760
tcacttcaac ctgcccacaa gctagtttcc actgatggta gaaaatcatc ttgccaattc  17820
acggtttgtc agtcacgttg gttttaaaac ttggtctttt ggaggtagcg gtgccattgc  17880
attcaagaac gctccttccc tcttttcctt tccttcccag tcaggctcat cagccctccc  17940
tccctacctg gtgccgtatt gctagagtca ccttgcattt ctccaagcgg acccacaatc  18000
tttcagctga ccagcacagt caccacgctg cacaaggcag gaggtgctgt ccaagttgta  18060
gtttgtgtga gttgtgcagt gcaccaactg gctgctggac tctatggccc ctaaattctc  18120
agattcctcc cacactatct agtgttgtca cccagagcca aggtgggggt gagcgtctca  18180
acccccttctc agggagggag gcagagttta aatccttgtt ataccctttcc ttaccttccc  18240
gtcttcccat cctgctggtc aaatgcttgc ttctttgttg gatggaggtg atgaggtcaa  18300
agtacagttt tcaaagaggt gaaatcatga ttctcataca aagatagagt gaccatgtgt  18360
caaatattta tttggctgat taatgggggga acgagtagaa tggtaaagaa tgcaagaaac  18420
tgatctattt gtctatctat ctatctatct atctatcatc tctgttgata tctgtctgct  18480
tgtctatcta gttatctaac tagctagctg tctattatct atctgtctgt ctctctgtct  18540
ctgtctgtct agctagctag ctgtctgttt atatctatct atctatctat ctatctatct  18600
atctatctat ctatctatca tcaatcatta atggaaaaag agaattgcta gaataagatt  18660
accaagttag atacaaacct ggttaaggtc ctaccaggca agaaaactca aacctttgga  18720
gttgtctttt ctagtgaatt aaaatcattg acagcttatt acagtcttct gaaagttaac  18780
atctacctct acagagtctg aggttgataa tctacaacca atagtaagtc agagatatta  18840
ctcctgagag cctcaggggg acttaatcag atgatgcttg gagacagaga ctggctcatt  18900
gcagcctgga caccgaatct ggtcaattgc tgcctgattt tgtatagccc atgagccaag  18960
aatgacatat atatatatat aacagagtct cactctgtca tccaggctgg agtgcagtgc  19020
cgcgatcttg gctcattgca acctccacct cccaggttca agcaattctc ctgcttcagc  19080
ctcctgagta gctgggacta caggtgcctg ccaccatgcc tggctaattt gtatattttt  19140
agaagagatg aggttttgcc gtgttggcca ggctggtctc gagctcctga cctcaggtga  19200
tccacctgcc tccacctccc aaagtgctgg gattacaggt gtgagccacc acgcctggct  19260
ccataggcca tttttcaatt attaaaaaat ataaaagtca gccaggcatg gtggctcatg  19320
cctgtaaccc agcactttgg gaggcagagg caggcagatc acctgaggtc aggagtttga  19380
gaccagcctg gccaagaagg cgaaaccccg tctcttctaa aaatataaaa attagccggg  19440
catggtggtg cgcacctgta gtcctaacca gtcaggaggc tgaggcagga gaatcacttg  19500
aacccggaag atggagcttg cagtgagctg agattgtgag gttgtgccac tgtactccag  19560
```

```
cctgggcgac agagtgagac tccatctcaa aaaaaaaaaa aaaaaaaaaa aaaaaagaaa  19620
gaaagaaagg aaaggaaaag gtcctatgga aagttatttt ttctcctgca atagaagtgc  19680
tatgtaatag cctcatgttg cctcgtgcct ctgtgtcccc atgttcctgg cagttgttct  19740
gtaattatct gtgctcagtg ggtgttcgtt tcatgaatga atgattgaac aaatgaatga  19800
aagcatgaat gaggagactg gttcagtgca tgtccagagc acagagtctc agggggcaga  19860
gataacaact caaatccttg aagtcgactt tatgagcact tccttcatgc caggccccat  19920
tcctgcgctg aggacaccag gatgaccgtg tcctcacccc tgccctcgga ggagctttaa  19980
gccccatgag ggagacagac acataaacag attctcataa caccaggtgc cagtgtgaga  20040
atagaggccc cagaggcagt ggagagaggg aattgttcgt tccaaagcag aagaggggc  20100
aaatcaagag cctcacacag agtcccagat ctacaggagg gaggggttgc tcctgactgg  20160
gggatcctgg aagacttcat ggagggggca tcagatttgg gcatgggccg ggcgtggtgg  20220
cacaagcctg taatcccagc actttgggag gccaagttga gcggatcacc tgaggtcagg  20280
agttcgaggc cagcctggcc aacatggcaa aaccccatct ctactgaaaa tacaaaatta  20340
gctggtcatg gtggcccatg cctgtaatcc cagctacttg ggaggctgag gcaggagaat  20400
tgcttgaacc caggaggtgg aggttgcagt gagccaagat tgcaccattg cactccagcc  20460
tgggcagcaa gagcaaattc cattaaaaaa aaaattagct ggacatggtg gtgtgcacct  20520
gtagtcctag ctactcgggg gtgggggtgg ggggctaagg tgggaggatc acccgagctc  20580
aggaggtcga ggctgcaatg agctgttgtg atcgcatcac tgcgctccag cctgagtgac  20640
aggctgtctc aacaataaaa taaaataatt ttcaaaagaa aaagaaattc aggcatgggg  20700
gtaggcagga atttgtcagg gcgagaagaa gaaagggttc cctgagcaga gggaatggca  20760
ggggcaaagg ctgggggagg ggaacaccca aggcgtgttc agttaattcc tcccagcccc  20820
gagaggtgcc aggctccctg aaggtgtttc tgattaacaa gaggttagca cacacctctc  20880
cacggaattc gtctcaaaaa aaaaaaaaag ggtaattatt aaagtggcaa gagcaaagaa  20940
tctgcttgga gcaagattta aagaacacaa aaccctagga agagccagcc atctttcccc  21000
agctgctggt ggaggccctg tcccttccct aggcagacat tgttgttctc tctctgggga  21060
ggtcagctcc ccactgcagt cagcatggcc aggggtcagg gagaaggggc tgagccacag  21120
gtggcagcat cagagcaaag tgtattcacc tccattccct tcctggtcct cagcactgcc  21180
cagaggaggt cataggacag ggattattat tacatccatt tgacagaact tggaatggct  21240
aagccactgg cccagactca gttaactacc cagaggtagt gaacatctac ctctacagag  21300
tctgaggttg ataatctgca accaatagta agtcagagtt attactcctg agagcctcag  21360
ggggacttaa tcagacaatg attggggaca gagactggct cactgcagcc tggacaccga  21420
atctggtcca ctgctgcctg attttgtatg gcccatgagc caagaatgac atcatcacac  21480
agctgatgag tgttggtgct aggtggggag ggtagtgccc ctccctcctt ctctccagtt  21540
ccctccccat atacccctc ccctgggggc ccagcagatg gcactagcct gggggcctg  21600
ccctcaggct gaccaagctg acaggggac ttttgcttgc ctgtggcctt ccaaagaaga  21660
cgatttaaag cagagaaaac agactgaaaa ctcaggtttt ataatttcat gtcaccaggc  21720
tgcctcccac atcccaggtt cattcctaaa tccccactgg ctcctggaag aacaccaggc  21780
ttctggcgag gtttaaatga gatactggat gctccacggg agagaacatg ttcactggca  21840
gaccctggtg cctagatcga acacacagtc ggtgcacagt cactgttttg aatgaatgaa  21900
```

-continued

```
tgaatgaatg aatgatgcag gtggtactgc tttgtaagtt ctagcagtgc atcagagctt  21960
acggattaga tggaagagca gagactcact ggtgtgtggg gtagggggt ggggtatgat  22020
ggtgaaacag ttgtgaagtg aggcagccgt gagatgggct aggtctgagc ctcaggcggg  22080
gccagctgca ggatgaaaag tcacaggcct ttctccccag ccctacctgc tccgtctccc  22140
tcacacccac ctgaggaacc aggcactgcc tttattgagc ccctactgtg caaggtgctg  22200
tgctgggcat tcaaacgtgt atcatcctac agcctctgct ggcggccctg caagggtggt  22260
gttatcgtcc cattctatag atgaggaaag caaggcccag gaaagattag gtggtggctg  22320
ggcaaaccca gatgtgtctg gcccaggtct gtgcaatgga cacaatcatt gaaagtatct  22380
catacagctg ttgtgggcat tgagcgagac agtgagggaa ggcattcagt tcagtttctg  22440
gcctgtagca aatgcttgat aagcacctgt tttattctga tggcttcacc atcattagct  22500
caaagctcat gtcctccccc cagggcagcc tcccagactc ctccttaggg cactcccttc  22560
tctctaccgg aagtgaagcc ctcatccctt cttctcctca ttgcctgtgg cctcgctggt  22620
ctccacagca gccagaggag tgtgtggtcc aagccagccc atgtccagcc ttgcccaacc  22680
ttctgtggct ccctatggct gcaggagaaa gcagcgccca tcctcggaat ggcctgggcc  22740
aggcctccct gccttcagct tgtcctctag atacacgtgc cctgtgtgta cttttctcaa  22800
agctgcccgg ctcgccccag cctctttgct cacgcaggga cccccaggat gcccccagcc  22860
cacaggccgg gtttgaagcc gtcacctcct gagctattct tgcctgttct gtgtctgtct  22920
gtccccgctg tcatccatgt ccccaggcag cgactggatt tttacctggg cactgagaag  22980
gcgtgaagct cagtgtgtgt ccattccatg agtgaatgac tgaaccaatg aacaaatgca  23040
tgaatgagga tactgacagg gaaagagaag gatggggtag agcatgtctg gctatcccca  23100
cccggctccc ctgcccagcc catcctgcct ggtggaggac cttgagggac ctggctcccc  23160
agggtcccct ccttctggct cacaggaatc aggggctgtg cccctctccc cgctccaggt  23220
tgttaccgct acagctacgt gggccagggc caggtcctcc ggctgaaggg gcctgaccac  23280
ctggcctcca gctgcctgtg gcacctgcag ggccccaagg acctcatgct caaactccgg  23340
ctggagtgga cgctggcaga gtgccgggac cgactggcca tgtatgacgt ggccgggccc  23400
ctggagaaga ggctcatcac ctcgtgagtc cctgggaagg agggcaggag ggagggctgg  23460
aaaagggagt ggttgatggg ggagttgaaa gtcacacaca gcattcttag acaagggagg  23520
gtaggacctt gggcctgggt atctgggaga caggacggct agcttagagg ggataggga  23580
gaggaggctg gagatggttg tgtactgggg gcgcttcccc tccgcgagcc tcagtttccc  23640
catctgtaac aaagccgttg ttgtagatga ctcctgaagt cagctctggg aggcaccgtg  23700
gcttgttggg atgtttcaga gtctggctgc agcctggact ttcaacctct gggctcgttc  23760
ctaaatcctg actgcttcct ggtagaacac ccaccctctc tgcttcccag gcttctggtg  23820
gggtttaaat gagatactag attccccatg ggaggggatg tcttcactgc cgggccctcg  23880
tgcctagacc aaacgcacag taggtgtgca gtatctattt tgagtgaacg aatgaatgat  23940
gtaggtggta ctgctttgca agttctagca atgcatcaga gctcacggat taaatgtaag  24000
agcagagagg cttactggtg tgtggggcgg gggtgtgggg atgtgacggg gaaccccctg  24060
tctcctagct gcgtgcccta aggcaagtta ctttgcctct tagaacctgc ttaccttgcc  24120
ggatcattgg aggatttaaa tcagactatc tgtgccatga tccttacaca tagtgagtgc  24180
ctagcactta cacgctagcc attattgtta tcattatata tgctctaact gggactgggc  24240
cgcaaaaggc attgagtgcc aggagccatt tggactttga tatttggtaa gtggggagct  24300
```

```
attgaaagtt cttgagcaca gaagtagggc tttagggcat aagatatgga gtggagtaca  24360
gaagtgatca ggatcagagg gcaggtggtt gggggtgggg aggagggact ggaaatggcc  24420
ttgacctctg ggagcctggt cctcccacag gatggggaga tgggtgttag cctacaaagc  24480
actgcaggag gtggggaaga tgctctgggc tgggcagttc tcagcgattg tttattgagc  24540
acttactttg tgctgggcgt caggctgatg cctcttctgt ctcacttggg ctgtggccag  24600
cctccaggca gatggggatg ggaccagtgt gttcagatca agcgcagtct ttgaatgtga  24660
gctggcagag gttcttgcca cacccctccc ccagggcctc tccaagctgc tctctccttg  24720
tcacccctcc tgctgtcctg ctgggtgtga cctcgatctg cggcatgtgc gtgggctgag  24780
tttctggagg gctctgggaa gtgcagagaa gccagacacc atctgacttc caggtccaaa  24840
aagggtgggg acacttaggg gtttcccctg gggcttctcc aggtgcctct cagcctggga  24900
ggggacctga ctgccaggcc cagctctgtt cctactcact gtggctcctg gtggctctct  24960
catcccagac ccttggagaa gctctaaaat gacaggtcag acaacatttg gggttctcaa  25020
gcttgtaccc cagacacctg ctagggaatg gggtgaggg ggactttggt ggtgatggga  25080
agacagagca ggtggcccct tgctcagttt caaccatgtg ctttgattct gcgttccata  25140
tttcatttat aagaagggct ctgccgctag gtaaataaaa taaaaccccc caacaatgaa  25200
agctaaagcc cccattaaag gtgacctcca ggtctcttcc atcctaatat cgtatctccc  25260
acctcccagg gaagatgagc cggtaaggcc aaaaaggacg tggctgtatg ggagggtggg  25320
gggcaccggt gtggttgggg agacttgggt gctgcagcag gaagatcaag ctggaatggt  25380
aggaagaagg gacgagggcc tggggggtga ggggggtggt gcctgctact ggaggccacc  25440
tccctcccct ggcaagaggc caggggaaat gccccatccc cggaccctgg gcaccaagac  25500
cctcccaggg agacccttgg ggttatgccc accatgcctc cagctggctg caggctgctt  25560
gggtgccatg tgtagcgatt ttgaggctgt gcttggagga gctcaggtac tcgcttgcca  25620
aggtgcctga aatccctcca gcagcacccc ttcctcctgt caaggcccag gtgcccacgc  25680
acagtctgca ggcagggagg ctattgggtt gcccattcag agggaggtgg ggccgttagt  25740
ttcttataaa ttgacccatc agatgcgctg gactccagag agtgttgcca ttgacactgg  25800
gaagtttggg ggaggttggt gagagggtga aggggagctg gggaacccct gtctgagaca  25860
ggcagaccag gggcacctac atatgtggga gggtaccagc catcacagac agtgcctagc  25920
gcaggcctat ctctgccatg gactgccggt agggcctcag tttccctatc tggaaatcaa  25980
gcagctgacc ccaacagtgt caccagtctt ttcagggctg acattccaga tttctaaaag  26040
cccagaagtc taagatacgg ttatttgttc cgagcctccc aggcgccaag ctctgggcag  26100
atttctgggg caccctgggg gtcacgagac cacacctgcc ttctccctgc ctatccttga  26160
gcacagccag gagtcgcggt gccagaaacg gtggtccctg cagatgccag tctagtcttc  26220
ctgccaggga cgctaggggt cacagatgat tctgtagcag ggtggagggg tctggggagg  26280
gagcatggga ctcgagccag ccgtcatcat caaactgtaa gctccagaag tctggggaac  26340
ctcctggcct ctctcacccg aggagctagc ctggtccttg gagggccttc agtctgtcct  26400
ctggggctgg ggagacacag aattctcccc acagacacac agtggtctct ggtaggagac  26460
ccggacccag aacccagatg tccagactcc cgtccaccct cccccagcag ccgcctgccg  26520
ccctccctgc cactcccctc ccagacccca gcccagcctt gccacctttc tgttctgcca  26580
gggtgtacgg ctgcagccgc caggagcccg tggtggaggt tctggcgtcg gggccatca  26640
```

-continued

```
tggcggtcgt ctggaagaag ggcctgcaca gctactacga ccccttcgtg ctctccgtgc  26700
agccggtggt cttccagggt gagaggtcag ggtccctgg ggcaggggag gggtggtggt  26760
agaatccaag ggccctccac tgggctcact gctcaccttt tttgcccaaa ttgaggatgg  26820
gatggggaga gggaagattc tggaagctcc tgctgctctc cactccccac cccggccccc  26880
ctcttccttc cgtcgtttgc acttccaccc ccctcttccc cttgaccgtc ctaccattcg  26940
cagtctctgt cttcctggca tcgctccctt gcttccctcc tctttctctg tccttccttc  27000
tctctccttt tctcttttct gtgctgaccg cctctcctcc ctcctcactc gcctggacct  27060
gtgtcccctc ccctctgccc ctcacccccct ccctgccctc tcccccttggc acccaccggt  27120
ggctgggcct ggaacacggg tctgtttgca gcaggactaa gaactccttg gattccgccc  27180
tagacagtcc gcttacagcc aagagggcgc agggagcttg gggaggtgtg atggcagcac  27240
agccaggcca tggccactgg tgtggcaggt ctcccactgc cttcccagcc cccaccctcc  27300
tcctgcttcg ggacctccct ccttgccccc ttcccaggaa gggcacgtcc caccccgcat  27360
gggacagctg tcctgggcct ggaccagcca tacttctgcg caggaggccc aaactttgcc  27420
atttctggag ctcaggaggg gaggatggca gagaggaggc catagagtgt tggcagctgc  27480
ttctgcctca cctctctccc cactcttctc cctcccactc agggtcccag ccctcttctc  27540
ggtttatccc caaactgtct ggcatagacc tgggtcccca gctggccaaa ctggagcgct  27600
aaatgggtag cagagctgtt cccttgggag tctgacacag gctcgaggcg ggagggaaca  27660
aagggctttg gggccctgg cccaatggag agatggccag ggcaggtgag catgctcctg  27720
tcctgacccc tggacccctc agcctctcac ggtgtagcct caaccaagcc actccttttc  27780
tccgaacctc atcttggaaa aggggaacag ctctctctcc cccagccacc accgtgaggc  27840
ctgtgcaggt gtgaatgcat tttgtaaact ggcgagtgct gtcccgcaaa tatcaataac  27900
taacacggat cgagcactta ctacatgcca ggctgtttga atgtttatgt ctttttaatc  27960
cactctacta ccctatgagg tgtgtgctat tactgtcctc attttacaga tgaggaaact  28020
gagacccaga ttcacacaat cacattcaac cacagcaatt tgctggcaga ggtggtaggg  28080
gtggtggggt tacaagctgc gccagcctgc tgggaggtgc agccagggga cccctgtgta  28140
acagctgctc tcctggtcca gcctgtgaag tgaacctgac gctggacaac aggctcgact  28200
cccagggcgt cctcagcacc ccgtacttcc ccagctacta ctcgccccaa acccactgct  28260
cctggcacct cacggtgaga ccccaccctg cctgcccacc tgccctctgc cgcaagcaca  28320
ctacaggtcc ctggtgaccc gggatgagag ggggcagtgt cccgcctctg ctgaagcgcc  28380
cacaggctga gccctgggta cacatcctgc cagggtggag agggctgtgg gcgaggtctc  28440
cctctgtggg tcacagcaat gcctgtttgt tgagtgactg acagacttta gccccacctg  28500
ggattctgtg tttccttctc tttgttgtta gggaggtggg ttcaccaacc tggccacacc  28560
ccatgggcca cctgatggcc cgctcctccc tcccaggtgc cctctctgga ctacggcttg  28620
gccctctggt ttgatgccta tgcactgagg aggcagaagt atgatttgcc gtgcacccag  28680
ggccagtgga cgatccagaa caggaggtac cacttcctct cctccctctg gcttcctttc  28740
ctccctcccc ctccctctct tccctcctca atagtgaccc cctcattgga agcccaagtc  28800
cccaatctca gaggggcagc aaggggagcg agcagaggct ggggctggtg tcaggcctgt  28860
tgcccttgac cttgtcctcg tcccagcctc cgccctggcc ccggcttccc ctctggctac  28920
cccagaggtc tcagacacgt ttggtcatca gacaccttgg atgtttattc taattacagc  28980
aaaattgtct catcttcttg ggtgctgtaa ccccctctgg caccctcaat ccttcaataa  29040
```

```
aatgtttcca gagccaaagg actcatgggc actttggtgc cttccctcta aacccaaggc  29100
gtaccatcag aggtgcctct ccccttatcac gaacccctgc tgcacagcca ggcccaatcc  29160
cattgcacag ggtaacatgg aaatcatggg tgccctggat cccccgaatc cccaacgggg  29220
cacttgccct cttccctgct cttgcccttg ctccctctgg taactaagtt tccgacaaag  29280
aagtgagtcc ttacagagat gtgagcaaga gacagtgggg ttaggctaag cgactaccgt  29340
tgccagggtc actatggcat gaggccagta ggtgcccact gggcctggcc accaggaagc  29400
catgggtggt gccgacagct tcagaggcct gggctgggca aggaggcagg gaaacagaga  29460
cagggtgtat ggacaggttt tcatttgtct gggaagaaaa gagaactagg aaattcaagg  29520
aaggggacat ttaagacggg agaggttcca tatctcaaat gtgtggatca tcccagcatc  29580
cccagaggga gagaaggagg ctcaggtgca ggtaatattg tttagagtgg ggagggtggg  29640
caaggggaga gggaggccct cccatggctc cattgttggg gagcagaggt ttggggagag  29700
agaagaggaa tattgaagca gcgatggcag agccagggag accctttccc tgggaatccg  29760
gggtgaaaac ggtcatcgtg tcagcgtcag gaaagaggag actctatcct tcatcgcagg  29820
ttgggcctct gccctccctt ccaacctcgg aattctgggg gcctaatggg ttcagagtct  29880
agtatgaaag atttgtcatt tcttgatttc acagagtttg aatatctaag atgccagtct  29940
tggaagatgc caaaattgga aggctctggg gctctagaat tcttggattt ctggggtgtg  30000
tgttcccaat caccaacact tgtaatttgc ttgttggctg atcctattca aaaggatcat  30060
ccagacaaaa ggtgacgaag aatgacaagg tttgcttgac tcctttttgc aatttatctg  30120
ggactaggat taaaagaaag gagaagaaat actcatggca tgatctaggg ctatgctgtt  30180
gggggtaaca tggggagtga ctttgggcct gtgctgttgg gggtgatatg gcgaagcagt  30240
gccttcaggg ctttgcattt ggtggtgata tgctgatgga gtgtgacatc aggcctgtgc  30300
tgctggggtg acatgctggt tcagtgatgt caggcctgtg ctgtctggag agcagaaggc  30360
ttctgtagca tgatgggggc acctctggga acggctgccc tgacccctca tggagctcac  30420
ttgaagcctc cttgctactc acctaggctg gggatggctg gcttcacccc cgctcacagg  30480
aacccgcagg gtgaccctga gatggatcca tgattcacag ttctgcgaat gatgagaaca  30540
tgttttcctg cctccctccc taccgcagag ctgaacttta tgtctcaggg aggcccacaa  30600
aggagaagga acagtcttgg gtctgacact ccctgtctca tccctcaccc ccttggcgac  30660
tccatttgcc agaggcgggg ccccagcatt caggggttgt ggggggttcg gtggcctgga  30720
gttaggtgct aagacaggcg ttcagtgcat tggcccaaca acttgtgtgg tcattggcgc  30780
cgttcctgtt tcccagagaa ggaaatcaag gctcagcagg attaggtggc acgcagatgg  30840
gtccacagat ggggtctctc ccatacccccc aacagccaca aacagcaggc caaaggatgc  30900
tccaccccat gcttcctgtg ggaaggccct cctccctccc tgatgcagtt gggcaagggt  30960
ctgggtactg gggagacagg gacttcgtga gctacccttg ggtaatgaca gagagagtgt  31020
ggaacacgga tgggagagtc ttttccctaa tccaaaggaa tgatgccttg atggtgaatt  31080
tgaggcacta ggacagcttc caacagggtg gagggatctc gccagagtct gagcaccact  31140
gagctataga atgtgtgggc tgaactggtc ctagcaccca acctatggta caggtgggga  31200
aactgggacc agcgagggct aaggacttgg cctcttgtcc ctgtcttttc tgcctttcag  31260
tggtggagat gggcttcagg gtgtagccaa gcggtggctg ggtggtgagg atgaggcctg  31320
acagctccct gtgcccccat agctccccct ctctctgttc agtcctccct cgccacacgg  31380
```

```
gggtggaagt gctcagcagg ggctggcatc agggtttgca tggatcccta gatgcacccc  31440
cttccttgtc tgtgaaacga ggggttcagg ccagcccagg gccccaatct ttgattgctt  31500
acccatcagg aagctattgt ctcccataca agttgtgttt attaattcct ggccaaacgc  31560
cattccaagt caggctggtg aggtggaaag cgcttaagtg tcgaagccag acaggccagg  31620
gctcagcacc tgtctcctct gcttcctacc tgggcgagga cttacatctc ccaacctcag  31680
gtaactcatc tgaaaaaagg gcgtgaaaga gaccccccacc ctgggaagac taagtgagac  31740
aacgcgtgga gaacattgca cacgcgggct taggtcaagt gcaacaaacc tgcgttcatc  31800
accggctctc actctgctct gggcaggcac aagctgaggg gtttatggtg ctggctcttt  31860
cagcctcaac aacccagcga ggaagcaggt gcctgtactg ccttcacaga ccagtgagac  31920
acccaagaca cagagagatg aagtaatttg cacaaagtca cccagctctt tgagccagag  31980
ttaaggccag gcagcctgat ctggagtgca cgtgggtgca cagatgcatg tctgtgtgcg  32040
tgcgtacatc catgcatgtc tgtgcacgtg tacgtgcatg tgtgtgtggt ccacgtgtgc  32100
gattcttccc tctgagcctc tagcggccca tgccagctgg tgactccctc agccaaggca  32160
tccccagcca acccactggc atctgggtgg ggggatcgac agtttctgtg gctgtcccac  32220
cagttccaga gcggcctggg aagtcccagc cctttcttct cagactttca ttaagggtcc  32280
agggtcccca ggggcagact cttgtcccct ccccgcagac tcctcctgtg tgaatgaatg  32340
tggaagggaa ggcagaggtg gcgcctgcaa accatccgca ctgggccact gtgccctcta  32400
gttatgatca tgggcgatag tgatcatccc atgtagatgc tgagaaattc ttagaatgag  32460
catttgttgg aaatctgctt gtgtgggtgg caaagacatg agaggtctag ggaagagcag  32520
attttcagac aaggcacttt agggaggggg aggtacagcc ctttggccca gaatgcccat  32580
tgatggagag ggcgggtcag gggagagggt atcttaaccc tcaagtgcca gcgtagtgat  32640
gaggaaaggc tggcctggtg ggccccccat ggactaagca tccttaggca cttcacctga  32700
ctcctctgag actgtggtgc ctccttcacc cctgacctgc ctgctttcta cctagcttct  32760
cccggtgccc acttgagccc agctgaggcc tcaggccctt gagtggcctg ggggtggtag  32820
agggacttgg cccgtgagat ctggccatgg ctgctccatt tcgcagaagc cactctcacg  32880
ggctgccacc gaagcacggg cttccccctt tccgggaacc tgcctcctgc cagcttcctc  32940
tcctgtgaca tcacttctct tgtgattcgc ccccaccattt ccactcactc ccagccagtg  33000
gggacaggca gaaccatggg ttccctaggc cagctggagc cacccccgac ccggcctggc  33060
ctggctatgg ggtggccctt gtgttctccg gagcgctagt ggccagcaca ggcggcagcc  33120
acagacactt agtaggaact tcagtgtggc tgacctgagc tgggctggcc gtgcaggaga  33180
gtgcaagctg cttcctccat gagctcacag cctgacgtca gcaagtgctt caaagaagtc  33240
atttcctatg catgccttaa accatgccac aagggagata cgatcacccc tgttttacaa  33300
atgtgaaaac taaagcttgc tgagggtgac ccaaggtcac acagcttgtt cctggggcaa  33360
agccaggctg ccaattcagc tctgcagccc caggtctaga gctctggcaa tgccaggtgc  33420
tgctctcctc ccctcttcag cacttgcctt ctgtgaccct ccttcccctt taatctgtct  33480
gtaggtaagg gcacgggggt gtgcattcat ccacccacgc acccttcttt ccttcttcct  33540
tcttgtgttc tccccaccct tccatccatc catccatcca tccatgcatc tatccctcca  33600
ggcagtacat cctgacaggg tccctgtcta cctcctggat gaggcaagaa ggaaatattc  33660
cccatatcca gagaggtgag gaagcaaggc aggccacacg gtgcaaaaat gtgccttcag  33720
acactcagta ctttgtagcc aagatgaact ggcaggcatc gcagcagtca ggcttctggt  33780
```

```
gcttcttgga gagggctaga ggggagcact tgttggacgg gaggcactgg agagccagag  33840
aatgtgcacc ctcccccaga gagttctgca gcagaaacag aaaactcaga tgggccaagg  33900
ggccaggcca gggctagagt ctatgatggg gggtagggta gtccagtggt gttttcgggg  33960
cttttctttc tttctctctt tctctttctt tctttctttc tttctttctt tctttctttc  34020
tttctttttc tttctttctt tctctttttc tccttctcct tctccttctt cctcttcttt  34080
ctctttcttc tttcttcttc cttattctcc ttttcccttc ttctcccttc ctcttctcct  34140
tcttctcctt ctcttccttc tcctcctcct ctttcttctt cttctccttc tcctcttcct  34200
cctcctcctt cttcttctcc tcctccttct cctcattctc tttctccttt cttcctcttc  34260
atcttttctt cttcttctcc tccgcctcct ccttcctctt cctcttcctc ttcctcttct  34320
ccttctaaag gagcaggaat ctggattatt atgtgaaatt agctcgcgac tcaatgaagc  34380
aatttctaca tggtgcataa acagattgtc tttacgctga gtgactccgc ttgggccact  34440
agatttcagc cgctgccttg aattcctctc tggcgctttc taagcagacg cttgttccag  34500
ggattccacc acctctaccc gtgctccagg cctccagagt gagaaccaaa cactgcccag  34560
acagacaggt tcccgggtac acggtgaggc cctggggaaa ggttgctgcc agctacagac  34620
tggttctagg actctccctg gaggttgaga gaacttcctg tagcaggcac aggtgtcttt  34680
gccttacagc ccctgcccaa ggcttgggtg acactacagg tcctcaacgc agttgcttct  34740
agggtgaaac gttccactcc cctccaaccc cggcttgggt tccttctctg tctccccaca  34800
atctccctgt gactgtggga agggacaccc caaggcccat gggatgcgct tgactcctca  34860
ttccccgcac tagtccttcc caacccctgg ctcccctgtc tacttcctga ggtccttctg  34920
tgaggaaaac aatccatgat aactttatag acaaacagac accaaaacct gcgtttcctg  34980
ggttttacaa gagcaagagg gccaggcttg ctcaggggcg ccccctggcg gtgcctcgtc  35040
ccccaccggc cctgctgggc tgggggaacc atggtcgggg gtggcggctc ccaacctgtt  35100
ctgcctcagg acccagtcac tctccgcaaa atgactgagt accctaaaga gtttttgctt  35160
atacaggtta tagatctata cttgcagcat tagaaattga aacaaaattt taaaatgttt  35220
attaattctt ttaatataat tataagccca ttacacattt gaatataaat aacattctat  35280
gaaaattagt tgcatcctcc aaaagtaaaa acatttagtg acaagagtgc tgtcatttta  35340
catttttgta catttcttta acaactggct tcacagacta caggcgggac cttcgaatct  35400
gcctccgagt tcaatcagtc ccgatgtcac acatcagtct ctggaaaact cgcctgtcac  35460
cttatgagag aatgagggca aaaaaggcaa atgatatctg agtgttacta taaacatgac  35520
ttttggaccc ccaggggtcc cctgactgtg ctttgagaac tgctggttgg tgtaagggta  35580
agatcgtggt cactgtggcc agatagactt agggggggtgc cagagtctag gccaggcgtg  35640
tggaggacat ggggcatgta gggggctcag acctcagagc tcctgttgca gtgggaattc  35700
ggagccctcc cctcaagcaa gctaggtgag ctcttctggg tcctgaggca agattctggc  35760
tccaccttgg ctcctgcact cttgagcctc atctgtaaaa tgggatgaga gcaattcctc  35820
cctccctggg tggaggtgct gcttgaacct cagaatcccc gtgcaatgag gccttgtgat  35880
gccatagcca atgaggctca gccccagcca cacacctgga gatgttaaaa cagcctcaaa  35940
gctcatcttc agctgttcgg tggctaagga attgattaac ttattgaacg gttaagtgct  36000
taccacattc tagaagttct ggggaagtgc ctggcccttg ggaatcatgg ccggctccgc  36060
agggtgttgg atttgctgtg ggatgtcccc actggccttc aggggcattc ctgatgctct  36120
```

-continued

```
ctggatttcc atctgctttc tctgccaggg gcattttcag ctctccctgc agattttcaa  36180
cctgcaccct gagtgtgttt cccccatctg caaagcactc tgatttgctc tgtggagggc  36240
atttctatga gctgatgaag ctgtccccat ctgttctgca agggtgtccc acctgggatg  36300
aaaaggaacc cccggctgct gtggagggag ggtcccactg tcctggggga gtggctgcac  36360
ccactctgtg aagtcatgcc gctgcccact tgctctgtgg ggtgaggtgc accggactct  36420
ctgcaggagg aacccctggg cccatgccct ggagatggga gggctcctac ctgttctctg  36480
gtaggagaga aagactcagc ctctctggag attcccccac ctgctctgtt tgaacaacgg  36540
tatcttcttg gtggtggtat ggcaggggtg caggggcggt gttgtccagc agggatgtga  36600
gggtgctccc acagctgggg gtggtcccac cccgtgtggc catgcacaga gaaggtgctg  36660
cccatcagca ctaagctact ggtcatggga gaaggactgg tccttccctc aagcccacag  36720
tgtcacaggg aggcaggagg gttggtgcct aaatggggag cactgctgcc ccctcgtccc  36780
acaccaagct caaggcagat gaccgtgcac atctgtggac agtggggcag tcaagggctt  36840
ttgcctcaac tgacacattg aagccttttg tcagattcaa gatcaacaga aataattttt  36900
cctttctttc tttctctttc tttcttttct tttctttttt ctttccctcc ctctctccct  36960
ttctttcttt ctctttctct ttcttctttc tttctttctt cctttctttc tctttctttc  37020
tttcttttc cctccctccc ttccttcctt ctttccctcc ctccttcctt cctaccttct  37080
gtctctttct ttcttttttt gacgtacttt cgttcttatt gcccaggctg gagtgcaatg  37140
gcacgatctc ggctcaccgc aacctctgct tcctgggttc aagcgattct cctgcttcag  37200
cctcccgagt agctgggatt acaagcatgt gccaccatgc ctggctaatt ttgtattttt  37260
agtagcaacg gggtttctcc atgttggtca gtctggtctc gaactcccga cttcaggtga  37320
tccacccacc tcagcctccc aaagtgctgg gattataggt gtgagccact gcgcccagcc  37380
aatttttctt gttttataag ggaggaaggt gaggctcaaa gaaggaccct gacttgctag  37440
aacctcacag ttcacaggtg actgtgacta gaattgagtt ttttatctgg caggcaatgg  37500
ggagccattg aagatttttg agcagggcag tggcatagcc aggctagttt ctagaagatg  37560
actctggggg tgcactcatc taagggagaa atcagggcag aggaggcaca gcgggcgtgc  37620
agctccccct gcccctctgg ctgcctgtcc ttgctctgtc tgtgcacggg acccaggaga  37680
ccagccagtg cagccctgag tcgtctctga ctccccccag gctgtgtggc ttgcgcatcc  37740
tgcagcccta cgccgagagg atccccgtgg tggccacggc cgggatcacc atcaacttca  37800
cctcccagat ctccctcacc gggcccggtg tgcgggtgca ctatggcttg tacaaccagt  37860
cggaccgtga gtatgggcag ccgggggaac cccctgcagt gactcgctgc ctcttggcca  37920
tccctggaac caccaagggg gctgtgggca gctgcttatg aggctgaaca aaaggagaga  37980
gagagtgtgt gtgtgtgtgt atgtgcttgc acaaatttat gcagctttgt gtgcccacgt  38040
gtgcaaggca gccacaaggg tttgcaggaa tacacactca tacatatcca cgtgtgtgtt  38100
gtgtattctg tgtgtgtgtc tggatatgta tgtctgcttg gactgtgtac acaggtgccc  38160
aggaccacgt ctgtgggtgc ctgtccatgc gcgtgtgagt gaacaggtgc atgcgtgtct  38220
ttgtgcgcct tcgcggctac gcatggccta atggcgccct gcctgcctcc acggtcccct  38280
gtggttttgc agcctgccct ggagagttcc tctgttctgt gaatggactc tgtgtccctg  38340
cctgtgatgg ggtcaaggac tgccccaacg gcctggatga gagaaactgc ggtgagtaac  38400
ccgcccgcgc atccctcctc tccctgccca tcccttctcc ttcctcacct ttcctgctct  38460
gagctgagtg gagaccccac ttctacatgc agcttccatt atgagcaccc aggaagtggg  38520
```

```
gttctctcac tgtgccgggg tggcaaaatg agacagacca gcaatgcagc ctccccgaga  38580
ccacctcgtg ggacagtggc agggagaagt ggggagccag gtctcctgac ttccagctca  38640
gggccatcac ccccagcccc tgtcccagcc agccttccag gaaggaacag aatgggtgag  38700
ggagatgtcc ccctcctctg ccctgtcaaa ggtttaaata tgtgggaaga gggaagcgag  38760
atgttcatgg tggggggatg atcctgccac ggtgctgggg gaggtacctc atattcagaa  38820
actgaacatc tggcttcaag ttctggctca gccaagtgac cttggacaag tcacctcatc  38880
tgtttccacc agtgaaatgg ggtatctcac agggttgctg tgaaactttg ggtgtaaaat  38940
agcagagaaa gaggccgggc gcagtggctc atgcctgtaa tcctagcact ttgggaggcg  39000
gagtcgagcg gatcacctga ggtcaggagt tcaagatcag cctggccaac atggtgaaac  39060
cccgtctcta ctaaaaatac aataattagc tgggcgtggt agcaggagcc tgtaattaat  39120
ctcagctact cgggagtctg aggcaggaga atcgcttgga cctgggaggt tgcagtgaga  39180
tcatgccatc gcactccagc cttcgtgaca agagcgagac ataaaaataa agtagcagag  39240
aaagagattt gtgattggta acgtgcaata cagcacacct tctacaggca tcgccaagcc  39300
ccggctggct cctctggctt cctcccacct gtcccctctc tgtgtcccca cacagtttgc  39360
agagccacat tccagtgcaa agaggacagc acatgcatct cactgcccaa ggtctgtgat  39420
gggcagcctg attgtctcaa cggcagcgac gaagagcagt gccaggaagg tagggcaggc  39480
ctagccgagt gtctggaggg acaccaaagg cagtctaggc ctgctacatg cttcagcaaa  39540
agtttctagc ttctcctctc aacacccacc aacccctctg tatttacatc tgtatgtctg  39600
tccattcatc catccatcca tccatccatc catccatcca tccatccatc catcttctgg  39660
tctccaatca ccgtctgtcc attgattcat acagctaccc atttatctat gcatctactg  39720
acctgtgcaa ccatcaatct ccctatcatc aaactgtcaa tctacccatt tattggtttg  39780
gctgactact ggtctatatg gccactgttc catccatcca tccatccatc catccatcca  39840
cccacccatc tacccaccca cccatccacc catccatcat ccatccgtcc atcatccatc  39900
catccatcat ccgtctatcc atccatccat ccatccatca tccatccatc cacccatcgt  39960
ccatccgtcc atcatccatc catccatcca tcatccatcc atcatccatc tatccatcca  40020
tcatccttcc acccatccgt catccaccca tcgatcatcc atctgtccat catccatcca  40080
tacatcatcc atctatccat ccatccattc atccatccat catccatgca tcatccatcc  40140
atcatccatc catccatcca tcatccgtct atccatccat ccatcatcca tccatccatc  40200
catcatccat ccgtccatca tccatccatc catcatccat ctatccatcc atccatccgt  40260
ccatcatcca tccatccatc atccatccat catccatccg tccatcaccc atccatccat  40320
catccatcca tccatcatcc atccatccat catccatccg tccatcatcc atccatccat  40380
cgtccatcat ccatccatcc atccatcatc catccatcca tcatccatcc atccatccat  40440
catccatcca ttcatccatc atccatccat tcatccatca tccatctgtc catcgtctat  40500
ccatccatca tccatcatcc atccatccat ccatccatcc atccatcatc catccatcca  40560
tcatccatca atccatcaat ccatcatcca tccatccatc atccatcgat ccatcatcca  40620
tccatccatg cacccatcca tcatccatcc atccatccat catccatcca ttcatccatc  40680
atccatccat ccatcatcca tccatccatc atccatccat ccatgcaacc atccatcatc  40740
catccatcca tcatccatcc atccatcatc catccatcca tccatcatcc atccatccat  40800
tcatccatca tccatccatc catcatccgt tcatccatca tccatccatt cacccatcat  40860
```

```
ccatccatcc atcatccatc catcatccgt ccatccatca tctgtccatc atccatccat  40920
ccatcatcca tccaaccatc catcatccat ccatccacca tccatccatt catccgtcag  40980
ccatccatcc atccatgcac ccatccatca tccatccatc catccatcca tcatccatcc  41040
atcatccatc catcatccac ccatccatca tccatccatc catctaccca tccatccacc  41100
catccatcca cccatccact gatctcccta gccccctgtc tgtccactgg tccttatatc  41160
cacacgttta tccaaccttc tagctgtctg tcagtctccc taatggacca ccactccacc  41220
cattggcttg tctgctcagt cttctgtctg ggtctattta tccatccatc catctaccca  41280
tccaactgac caactgacca acacttgcag gctacccagc gataggcaag gtgcagtaag  41340
gaagtgagaa taaaacagca gagatgcagg ccctgccttc caaggctcat ctgttagtag  41400
gaggatatga tgggtgactc tcctgccttg taggaagatt ggagggcagg gaggaggtca  41460
gacatgaaaa gcttcctgga ggaggtaggt gtttggccct tggtgagagc taaaacttaa  41520
ataggcagga ggaaaggaga gaggcaaaga ccaagtggtg gagtggaaag ttctttacag  41580
tgaagagcag ggaggaaaat gtggacaacc gggcagggcc agagcctggg agattgccag  41640
gctaggtgcg gaccctggtc taaaagtgga ggcacagttc tgccttcaag ttccacactg  41700
gagggggagg catgatcttg tggtcaggat ctccagtctg agaatggaga caccactttg  41760
tgctcaatag gccagtctga gtggaggggc tgtggggggc gggggggacat ggcctgcttt  41820
taggagaccc taaaggagac tcaggaaaag actctctagt cacctcctgg ctcttctggc  41880
tccatcgttc ctgcacccca ctttggaagg tttccttggg gctcagagac ccaccttctg  41940
tgccctgccc ccatcccctc tgtcccaggg gtgccatgtg ggacattcac cttccagtgt  42000
gaggaccgga gctgcgtgaa gaagcccaac ccgcagtgtg atgggcggcc cgactgcagg  42060
gacggctcgg atgaggagca ctgtggtgag ccctgcctgg ctgccggggc cctggagctt  42120
gggagggagg gggtgcccac agcaggaagc tggagggaaa tctcactgtt gtcccctggt  42180
ctctctctat ctcatcctct gccccccttgc ctgggtcctg atggtctctc cccctccatc  42240
attctcctgt tctctgtctc tccatctctt tcctttgccc ttcctctctg tctgcttctc  42300
cccttcccct cctcctctgt ccaccccacc acctgccccc atccccagac tgtggcctcc  42360
agggcccctc cagccgcatt gttggtggag ctgtgtcctc cgagggtgag tggccatggc  42420
aggccagcct ccaggttcgg ggtcgacaca tctgtggggg ggccctcatc gctgaccgct  42480
gggtgataac agctgcccac tgcttccagg aggacaggtg agcgggaggg tgtgggggcc  42540
taggcagtaa gagacaaggg cagggaaggc ccggtgggag gtgcactgtg tctgagctct  42600
ttgcagatag agggaagggt ggtggacccc ccagacaggc tactgtgatg tgagttctag  42660
tcctggctcc accaggacct tctgggtccc cggacacatt gttccacctc tctgccatct  42720
acttttggta tcttgcttta agttgggcca gtaattcatt cattcatctc attcactcat  42780
tcagcaacac ttgtgctcct actatgtgcc agggctgtgc tagatgctgg ggattcagta  42840
aaggacagaa ctgcccaacc tggtcataag ctatgacact ccccgaggtg tgacacgagg  42900
tagcaggtgg ggctggggag cccccagggg acatctcatc aggcctcatg gccatctttc  42960
ccatctgctt ggtgggctga aacctccccc aatccacccc cagacagatc tgggctccag  43020
atcccgcccc caggccctgc acagggatcc ccttttgtat cctctctggg acgcagggcg  43080
ctctgaccac ctagctctct ttaaccccat ctcaggctcc ccactgccct caggtagagg  43140
gtagagaccc gaaggctgcc catctgccac ccaggcagct gactgccgca gtccaattcc  43200
tccacgctca actcccaccc gctccccact aggacccacc agcctcaggg aattcagagc  43260
```

```
agcctgggtc tgtaaagcac acaggaaaaa agaaatctgt gtcgggggcc tggcactgtg  43320
ctacattttt tagatacacg gtcttattgg attctctcaa gaacattcga gtagaaaatg  43380
ccattcccat ttgcagatga ggtggcagag gcttagagag gcacacccat gtctagggag  43440
ggatgaagct ggggcgtgga acccaggcag gccgagtggg tgaaggctga acgctgtacc  43500
accagctagg cgaccttcag ggagggaagg gagggctggg tgtggagggc actgtcccgg  43560
gcggggatct ggctatcttg agggtccctg gatggggaga ggcagcttcc tcccacctca  43620
cctcacccca ccccacccca ccccacccca ccccagcatg gcctccacgg tgctgtggac  43680
cgtgttcctg ggcaaggtgt ggcagaactc gcgctggcct ggagaggtgt ccttcaaggt  43740
gagccgcctg ctcctgcacc cgtaccacga agaggacagc catgactacg acgtggcgct  43800
gctgcagctc gaccacccgg tggtgcgctc ggccgccgtg cgccccgtct gcctgcccgc  43860
gcgctcccac ttcttcgagc ccggcctgca ctgctggatt acgggctggg gcgccttgcg  43920
cgagggcggt gagcagcggg gacttgcggc gggaggcgga gggagaccgt gcggatctgc  43980
gccgtaacac ctggcctgga gaagggcggg gctgggggtc ccggggctcc accccatagg  44040
ccctctagtg ctgggattca aattgggctg aattttacgg tagaaaacca ccatttaatg  44100
cggcctgtag gcccctgccc ctcccctcct agctcttccc ttccttctgg aagggcgtta  44160
tgtgtggggc aaaggggcag gtctgggacg ccactgccca cgtgcaagct ccacctgctg  44220
ttccttgggc tgcaagggtg gaaggctctt aattactagc actttccaca tccaggctgg  44280
attttagggg aacttgactt catataatcc acccaacagc cctacgggcg gatgctgtgg  44340
ccctatttta tggatggaga aaccaaggct cagagacatg ttgctgtaag tcacacagcc  44400
agagaggact ggagcaaaga ttagaaccca gggctggctg cctccagagc ccctgctctt  44460
cctgctactg ctctcagaaa cagggtctct cccctttcta cgttcactga ccagagtccc  44520
tggcggccac cgcacagttt tggggacaca gacccagctg gcaaacctac agacatgccc  44580
tgcagcgtta gtgttggtgg cttcaaaaat gtgtacagtg acttacaatc tggaagcagg  44640
cggggccgca gagatatttt aaggatgggg aaactgaggc tcagaggaac agtgacttac  44700
ccaaggggat ggcagtggtc atggcaaagc aaaggctggt tcattcacta ttccttcact  44760
cattcagtca ctcaatgaca ctttctgagc accaagtacg taccaggcgt ggggttaggg  44820
gaagggtaca taaggatgaa gagagaacat tctcgggggga gacagacagt ggtaagagct  44880
gacatggatg gggagatgca ggaacagtgg agacacagag gaggctcctg cccagctagg  44940
gtcaggggag gcttccaggg gagggttgtt taagctgagg cctggaagat gagttggcaa  45000
cattcagaca aaggggaaag acattcaggt gaagacacag gtgccaagac aggaagatgt  45060
gagaacatcc gcagcctgcc agaggggctg aggtgggggg caggcgtgcc tgggcgagga  45120
gcaaccagaa tggcagacag ggccttgggc gaggagcaac cagaatggca gacagggcct  45180
tgccggccag cataaggatc ttaggccagg agttctccct cctacctgca ccttagaacc  45240
atacggggag tttcaagaaa aactgcgtat caaggctccc cgggggactg tgatatgcag  45300
ccctcgtgga gaagcgctag ggcagactgc agagttgggg cactgcagag ttctaaggaa  45360
accatgaagg gatcagatgt gggcttcgga gacatctgca ggtgctgtaa cagagcagcg  45420
aggagccagc cagagcccag aggtgcctca gcagacagag gtgggggaca agaagctgga  45480
ggaagacact catccacacg ggcttttttc ttttttcttt tttttgtttt tttgagacag  45540
agtttcgctc ttgttgccca ggctggagtg caatggcgcg atctcggctc ggatcccccct  45600
```

```
cctcccgggt tcaagcggtt ctcctgcctc agcctcctga gtaactggga ttacaggcat  45660
gtgccaccac acccagctaa ttttgtattt ttagtacaga cagggtttct ccatgttggt  45720
caagctggtc tcaaactctt gacctcaggt gttccgtccg cctcagcctc ccaaagtgct  45780
gggattacag gcatgagcca ccgtgcccgg ccctccacat gggctttggt cgggggctgt  45840
caccatgaac cccacagaga aagagctaga ataaagtgac agggaggcag aggggcaggt  45900
gcgaccctag caggggtaag ggtgggcaga gcaggagaga agtaggctcc tgagatgcaa  45960
agggaataat gttagggaga atagagaaca ggggctccag gctcctgaga tctcacttct  46020
gcccttgacc acggacaggc cccatcagca acgctctgca gaaagtggat gtgcagttga  46080
tcccacagga cctgtgcagc gaggtctatc gctaccaggt gacgccacgc atgctgtgtg  46140
ccggctaccg caagggcaag aaggatgcct gtcaggtgag tcccccgggc atgggaggga  46200
gagaggaggg agaaaggatg ctgcccacat caccagggtc tggccctttg ctcacatcag  46260
cctgctgaag cctcccatcc tcccagcaag gtggtgatgg ccacccctac tttacagaag  46320
aggagactgg ggcttagaaa ggttgaggag cttgcccaag gttgcagagc cacagatcag  46380
aagagatgct gtgatgggca ggtgttaggc tcaaacccag ttctgctcct tgcccaccac  46440
aaggcactag gcccagggtc ccacagtgag gtggatgcat ggaagaagaa aggggtgtca  46500
gccacagaag ggaggcggag gcagagtggg ggcgtgggga cacagccaca gttccaggag  46560
gtcccaggct ggctggaggc cggggagggc tggcttgggc tctctccatt tagcaggcga  46620
ggggaaagca gagctttaag actgaacgtg actctggcac ccagtcaatt cccaacagtc  46680
aggacttaat ccctatggct cttcacctgg aaaagggggt gcccttaccc tgcttcagtc  46740
ctttctcctt tccccctttc agggtgactc aggtggtccg ctggtgtgca aggcactcag  46800
tggccgctgg ttcctggcgg ggctggtcag ctggggcctg ggctgtggcc ggcctaacta  46860
cttcggcgtc tacacccgca tcacaggtgt gatcagctgg atccagcaag tggtgacctg  46920
aggaactgcc cccctgcaaa gcagggccca cctcctggac tcagagagcc cagggcaact  46980
gccaagcagg gggacaagta ttctggcggg gggtggggga gagagcaggc cctgtggtgg  47040
caggaggtgg catcttgtct cgtccctgat gtctgctcca gtgatggcag gaggatggag  47100
aagtgccagc agctgggggt caagacgtcc cctgaggacc caggcccaca cccagccctt  47160
ctgcctccca attctctctc ctccgtcccc ttcctccact gctgcctaat gcaaggcagt  47220
ggctcagcag caagaatgct ggttctacat cccgaggagt gtctgaggtg cgccccactc  47280
tgtacagagg ctgtttgggc agccttgcct ccagagagca gattccagct tcggaagccc  47340
ctggtctaac ttgggatctg ggaatggaag gtgctcccat cggaggggac cctcagagcc  47400
ctggagactg ccaggtgggc ctgctgccac tgtaagccaa aaggtgggga agtcctgact  47460
ccagggtcct tgccccaccc ctgcctgcca cctgggccct cacagcccag accctcactg  47520
ggaggtgagc tcagctgccc tttggaataa agctgcctga tccaagcccc gctgctggag  47580
tttgaatggg acccaggcac cagcctcatg cccttgactg gagcagcccc tgcttcctgc  47640
tcagcctgtt tgacaagtgt ccagaaggcc aaggtgggct cagtggcagt gggcgtggcc  47700
actgagggct ggggcctgca gggcagctgc ccaggtccca gaagaaatgc caggaaggca  47760
atcatttggg gaccctcagg tcagagggat gtgaggagca atcgtctcct tttggaacct  47820
taggaggaaa ctgaggctca gagaggcggt taagacatcc tcatagtggc actgggggtt  47880
aggagtggag gtggcataga ctcctgtctc ccagctccct gtctgccaag gccccgtcca  47940
gtgcgacact cccttccttt gcattctttg agccactgaa taaagccttg ggctccaacc  48000
```

```
atgtgccagc actatgctgg ggccacaggg gtgaaggacc tggctcctga ccccaggagc  48060
agtggggatg atccagtggg aaggggccgg aggggagcgt ggactgggca agtcaaggca  48120
agctgcctgg aggctgtgag acttgagctg gggttcagag gtggtccagg tgggaatatc  48180
cgggaaggat attccaggca gggaagagca cgtgcaaagg cacagtcccg gaagaatgag  48240
gcacgctagg acccagcaag ccgagtgagt gttagaacag agctcgagag gatgactcaa  48300
gaattcagag gggcgaactg aggcgggata gcagagcctg gggttgagcc aaggatttga  48360
tcttgaaagc tctggggagc cacggtgggc tctatagcat aggagtgaca tgagaggatt  48420
cacattttgg aaccagcctt ggcaccagtg tgcagggagc ggcaggcagg gaggctggtt  48480
aggaggccac cgcaggattc caggatggag aggatgggcc gggactgagc agcgccatgg  48540
gatggactgg aggatgattt tagacccctg ggggcagttg tgatggaggc agggggctcg  48600
ctggaggtga gggtggacgg tcaagtgtgg acaactcttt ctagacgcct aactgggagc  48660
ggaagggaga gagggagctt cagaggggcc ccagactgaa gaggggtttt tccaacatgg  48720
gcgctgctgc caggtctgtg ggtgaatgag gcagaagggg aaccagggac ggggagcacc  48780
cacctgggtc ctgccaggac gagccggagc agctgggtgg gcagggagcg tctccagagc  48840
aggtgggcag aacacatgca gaataccttg ggtgatctgg aatcaccctg ggccctacct  48900
cagtcttcat cggaatcctg gagggcgggg gacgtgtcat ctgttctcct aacaagcctc  48960
ctggtgactc ttttgcaagg atagttggac cctaaaaatg agtccagctt tggagtggag  49020
tgtcctcagg ggaagtggcg aggccctcca ggcttgagct ggcaagaggg tgccccccgcc  49080
ccagcctgtg gaaggcctgc gccttagggg ctcactgccc ggcaggattt cctcgagcag  49140
cggggaggac tgaggagttg aaggaactgg ccagggtggg tggagggtct ggggtctggg  49200
ctgggtccag cagggtcaga gaagggagag ggcggggtgt ttatatttcc taggattttg  49260
ggcagagggg tggcagcaat agggagggat ggcggtggcc caggtgtcag agtagaagtg  49320
gagggggcgc gctgagaggt ttaggatgtg gcagaggcag cccagggctc tccctagagt  49380
tctgttttct ggctcccggc caggtagggc aggtgctctg gtatccggcc ccagggcaaa  49440
ggatatagcc agttccccaa gccctccctg caacacacac aggaaaatga caacagggca  49500
gcgtccctgg gcttttggga caaagccgcg ttcctttgga ccagactacc acacctttag  49560
tttagccccg tccccaaaag tggcccagag aaagagggca acagccaggc tgggctgttc  49620
ctttgggttt tattacatgg tggggtcgga cacagctgag aagcaaggac ccatcccggg  49680
aagtcaaaca caggagggcc cctggctcag ccgccatacc cactctcccc gggcagttcc  49740
tgagtcctcc accgcccctg cccagcccct tctgctgcct ctccccgccc cccaggccag  49800
gcgctgggcc agcaatgcaa atggctgggg gtgggatcac caaagagaag gccaagccaa  49860
ctacccctac tctgccaggc cagctcccca caacctgcat ccccaatacc tgaatctcca  49920
tttgcaaaca cagtgttatg cccaggggtc gggctgggtc cttcccatcc cagggcagct  49980
gaaggtgggc ggcccctata tactgcctga gggccttcag ggactttgct cctctgtgca  50040
ccctcacaac aaccctgtga ggtaggtggg gtgggaggag tgaccccctg gactaaggct  50100
caaggaggca atgtgaccgg gccaggaagg agcacatcca ccatgcagca ggggagcccg  50160
ggagagggga cgcaggtgcc ggagagacac agccagacat tgccacacat ctgccatgag  50220
cagtccactc tgcccagagg tcctggggcc caccttgggc cttaagaggt cccagggggg  50280
ccccgccccg cccctggagg caggagtaag tcacagcccc acgggtgcag acagaggagg  50340
```

ccggggagag ggtgcttctt ccttctcagg cccggggccc accccatggt acaaaaataa 50400
aggatttcag atgggaaccc caagtccctg gaggtgatct ggggcctcac atccgggtgc 50460
ctctggcttg taacagctag aaaaaaaaga ggggaagggc aggaggatgg gaggggcgga 50520
ggtggggccg gtaaggaggg ggtgatgcag ggcaaggggg cggagaggag attgacgggt 50580
gggggagagg gagagagaga gaggcagttg agtcacaggc ttccttctgg aggagggggt 50640
ggggctgagg cccaaagaag gtggattcag aactgagttg gggggagcag caagggctcc 50700
ccaactaacc catccaggag ccccatgccc cgtcttgggc tcggtggcgg ccacctacag 50760
aggccagatt ctgccaagac tctgaagggg gtgggatggg ggttgctcag ggctgggaga 50820
ggcactgatg ccccaggcga aagaagccac agggagcagc tgtctgtccc aattttagag 50880
gcaattgtgg cccagagagg gacagtgact tgcccaaggt cacagagcag gcagaaaaga 50940
gtgggatagg gggcttgtgg gcacatggcc agggcttttt ctgccactct gcaatcctta 51000

<210> SEQ ID NO 2
<211> LENGTH: 3209
<212> TYPE: DNA
<213> ORGANISM: Homo sapien

<400> SEQUENCE: 2
cttgagccag acccagtcca gctctggtgc ctgccctctg gtgcgagctg acctgagatg 60
cacttccctc ctctgtgagc tgtctcggca cccacttgca gtcactgccg cctgatgttg 120
ttactcttcc actccaaaag gatgcccgtg gccgaggccc cccaggtggc tggcgggcag 180
ggggacggag gtgatggcga ggaagcggag ccggagggga tgttcaaggc ctgtgaggac 240
tccaagagaa aagcccgggg ctacctccgc ctggtgcccc tgtttgtgct gctggccctg 300
ctcgtgctgg cttcggcggg ggtgctactc tggtatttcc tagggtacaa ggcggaggtg 360
atggtcagcc aggtgtactc aggcagtctg cgtgtactca atcgccactt ctcccaggat 420
cttacccgcc gggaatctag tgccttccgc agtgaaaccg ccaaagccca gaagatgctc 480
aaggagctca tcaccagcac ccgcctggga acttactaca actccagctc cgtctattcc 540
tttggggagg gacccctcac ctgcttcttc tggttcattc tccaaatccc cgagcaccgc 600
cggctgatgc tgagccccga ggtggtgcag gcactgctgg tggaggagct gctgtccaca 660
gtcaacagct cggctgccgt cccctacagg gccgagtacg aagtggaccc cgagggccta 720
gtgatcctgg aagccagtgt gaaagacata gctgcattga attccacgct gggttgttac 780
cgctacagct acgtgggcca gggccaggtc ctccggctga aggggcctga ccacctggcc 840
tccagctgcc tgtggcacct gcagggcccc aaggacctca tgctcaaact ccggctggag 900
tggacgctgg cagagtgccg ggaccgactg gccatgtatg acgtggccgg gcccctggag 960
aagaggctca tcacctcggt gtacggctgc agccgccagg agcccgtggt ggaggttctg 1020
gcgtcggggg ccatcatggc ggtcgtctgg aagaagggcc tgcacagcta ctacgacccc 1080
ttcgtgctct ccgtgcagcc ggtggtcttc caggcctgtg aagtgaacct gacgctggac 1140
aacaggctcg actcccaggg cgtcctcagc accccgtact tccccagcta ctactcgccc 1200
caaacccact gctcctggca cctcacggtg ccctctctgg actacggctt ggccctctgg 1260
tttgatgcct atgcactgag gaggcagaag tatgatttgc cgtgcaccca gggccagtgg 1320
acgatccaga acaggaggct gtgtggcttg cgcatcctgc agccctacgc cgagaggatc 1380
cccgtggtgg ccacggccgg gatcaccatc aacttcacct cccagatctc cctcaccggg 1440
cccggtgtgc gggtgcacta tggcttgtac aaccagtcgg acccctgccc tggagagttc 1500

```
ctctgttctg tgaatggact ctgtgtccct gcctgtgatg gggtcaagga ctgccccaac   1560

ggcctggatg agagaaactg cgtttgcaga gccacattcc agtgcaaaga ggacagcaca   1620

tgcatctcac tgcccaaggt ctgtgatggg cagcctgatt gtctcaacgg cagcgacgaa   1680

gagcagtgcc aggaaggggt gccatgtggg acattcacct tccagtgtga ggaccggagc   1740

tgcgtgaaga agcccaaccc gcagtgtgat gggcggcccg actgcaggga cggctcggat   1800

gaggagcact gtgactgtgg cctccagggc ccctccagcc gcattgttgg tggagctgtg   1860

tcctccgagg gtgagtggcc atggcaggcc agcctccagg ttcggggtcg acacatctgt   1920

ggggggcccc tcatcgctga ccgctgggtg ataacagctg cccactgctt ccaggaggac   1980

agcatggcct ccacggtgct gtggaccgtg ttcctgggca aggtgtggca gaactcgcgc   2040

tggcctggag aggtgtcctt caaggtgagc cgcctgctcc tgcacccgta ccacgaagag   2100

gacagccatg actacgacgt ggcgctgctg cagctcgacc acccggtggt gcgctcggcc   2160

gccgtgcgcc ccgtctgcct gcccgcgcgc tcccacttct tcgagcccgg cctgcactgc   2220

tggattacgg gctggggcgc cttgcgcgag ggcggcccca tcagcaacgc tctgcagaaa   2280

gtggatgtgc agttgatccc acaggacctg tgcagcgagg tctatcgcta ccaggtgacg   2340

ccacgcatgc tgtgtgccgg ctaccgcaag ggcaagaagg atgcctgtca gggtgactca   2400

ggtggtccgc tggtgtgcaa ggcactcagt ggccgctggt tcctggcggg gctggtcagc   2460

tggggcctgg gctgtggccg gcctaactac ttcggcgtct acacccgcat cacaggtgtg   2520

atcagctgga tccagcaagt ggtgacctga ggaactgccc ccctgcaaag cagggcccac   2580

ctcctggact cagagagccc agggcaactg ccaagcaggg ggacaagtat tctggcgggg   2640

ggtgggggag agagcaggcc ctgtggtggc aggaggtggc atcttgtctc gtccctgatg   2700

tctgctccag tgatggcagg aggatggaga agtgccagca gctgggggtc aagacgtccc   2760

ctgaggaccc aggcccacac ccagcccttc tgcctcccaa ttctctctcc tccgtcccct   2820

tcctccactg ctgcctaatg caaggcagtg gctcagcagc aagaatgctg gttctacatc   2880

ccgaggagtg tctgaggtgc gccccactct gtacagaggc tgtttgggca gccttgcctc   2940

cagagagcag attccagctt cggaagcccc tggtctaact tgggatctgg gaatggaagg   3000

tgctcccatc ggaggggacc ctcagagccc tggagactgc caggtgggcc tgctgccact   3060

gtaagccaaa aggtggggaa gtcctgactc cagggtcctt gccccacccc tgcctgccac   3120

ctgggccctc acagcccaga ccctcactgg gaggtgagct cagctgccct ttggaataaa   3180

gctgcctgat ccaaaaaaaa aaaaaaaaa                                     3209

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3

ctttattcca aagggcagct                                                 20


<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 4

gcttagagta cagcccactt                                                 20


<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5

ccttccctga aggttcctcc                                                 20
```

METHODS OF IMPROVING ANEMIAS BY COMBINING AGENTS

This application is a § 371 application of PCT/US2019/029794, filed Apr. 30, 2019, which claims priority under 35 U.S.C. § 119(e) to U.S. Provisional Patent Application No. 62/664,327, filed on Apr. 30, 2018. The foregoing applications are incorporated by reference herein.

SEQUENCE LISTING

The present application is being filed along with a Sequence Listing in electronic format. The Sequence Listing is provided as a file entitled SeqList.txt, created Apr. 30, 2019, which is 72 Kb in size. The information in the electronic format of the sequence listing is incorporated herein by reference in its entirety.

BACKGROUND OF THE INVENTION

Several publications and patent documents are cited throughout the specification in order to describe the state of the art to which this invention pertains. Each of these citations is incorporated herein by reference as though set forth in full.

Erythropoietin (EPO) is a hormone that stimulates the production of red blood cells and is one example of an erythropoiesis stimulating agent (ESA). EPO and other ESAs are used to treat some types of anemias.

Certain types of anemias are associated with iron overload. In such instances, treatment may include iron chelation, which eliminates or limits excess iron from organs but does not prevent iron absorption and does not improve red cell production.

There is a strong correlation between erythropoiesis, red blood cell synthesis, and iron metabolism, all of which may be affected by any treatment for any type of anemia.

SUMMARY OF THE INVENTION

The present disclosure provides methods of administering an erythropoiesis stimulating agent (ESA) and an iron restrictive agent (IRA) to a subject. In certain embodiments, the subject has, or is at risk of having, an anemia. In certain embodiments, administration of the ESA and IRA treats the anemia. In certain embodiments, administration of the ESA and IRA mitigates one or more symptoms in the subject. In certain embodiments, administration of the ESA and IRA mitigates the one or more symptoms to a greater extent than the mitigation provided by administration of one agent alone. In certain embodiments, the IRA is a TMPRSS6 inhibitor.

DETAILED DESCRIPTION OF THE INVENTION

Figure 1:
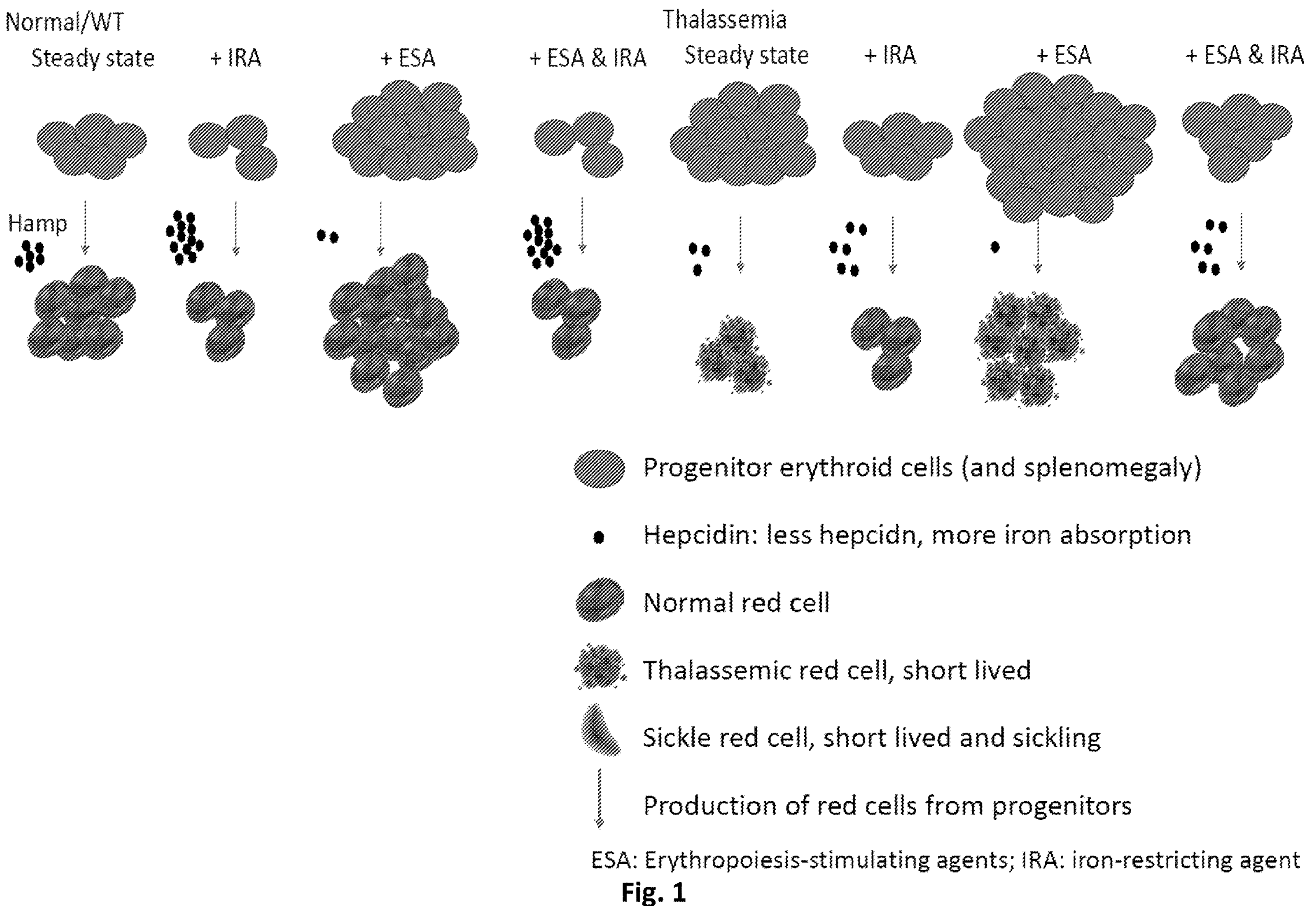
FIG. 1 shows a comparison of red blood cell production, amounts, and quality in wild type and disease states as well as effects of various treatments and combination treatments.
Figure 2:
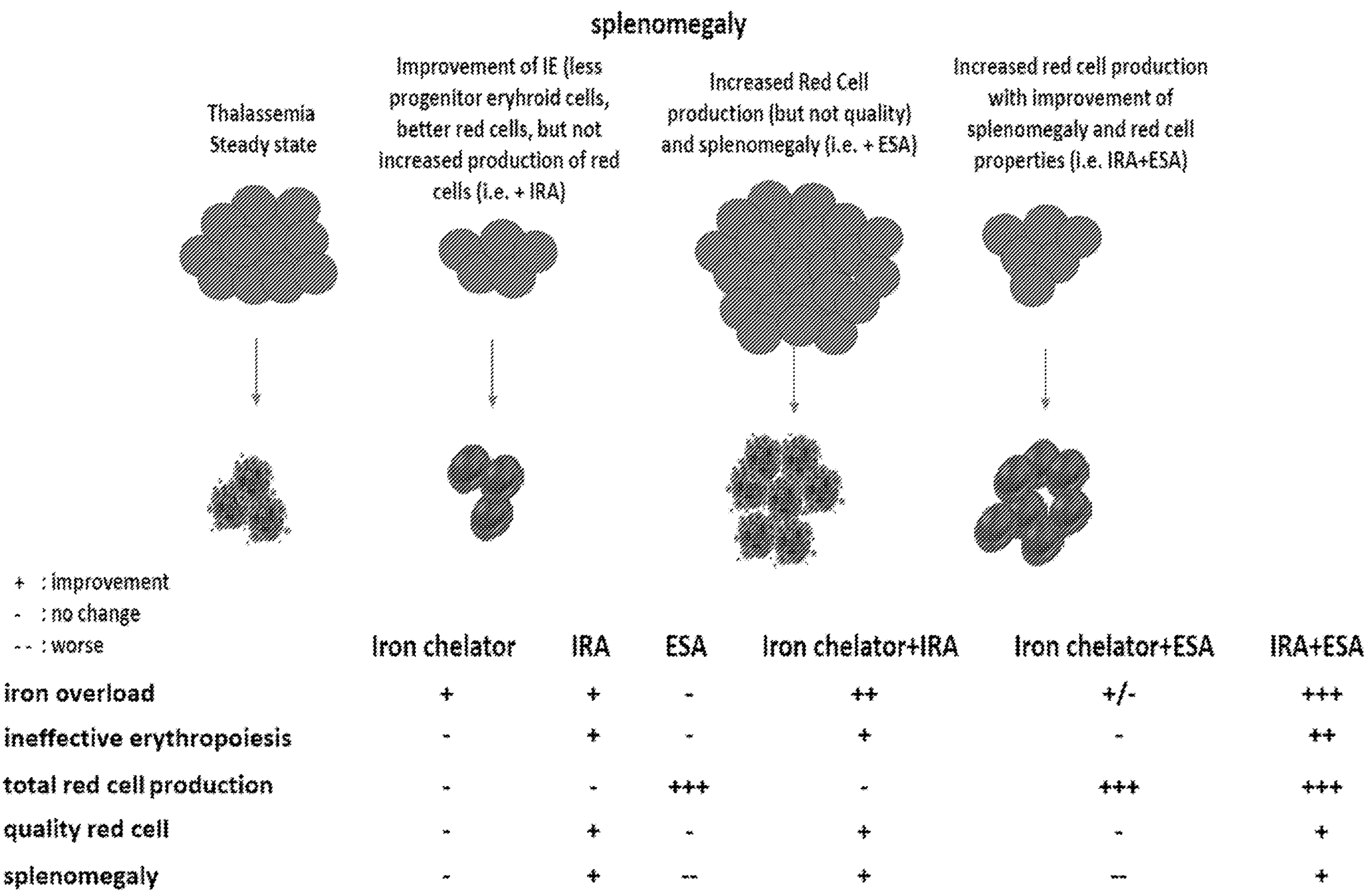
FIG. 2 shows a comparison of the effects of various treatments and combination treatments.

Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described.

Definitions

As used herein, "2'-deoxynucleoside" means a nucleoside comprising 2'-H(H) ribosyl sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, "2'-fluoro" or "2'-F" means a 2'-F in place of the 2'-OH group of a ribosyl ring of a sugar moiety.

As used herein, "2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

As used herein, "agent" means a compound, pharmaceutical composition, one substance, or composition comprising multiple substances.

As used herein, "anemia" means a disorder in which production of red blood cells is adversely affected. Examples of such adverse effects include underproduction of red blood cells and production of abnormal red blood cells. Polycythemia is not an anemia. Anemia can occur with or without an iron disorder. Anemias include thalassemias (e.g., β-thalassemia (e.g., major β-thalassemia)).

Some forms of anemia are associated with iron overload and include but are not limited to thalassemias and certain forms of myelodysplastic syndrome (MDS). Other forms of anemia are not associated with iron overload and include but are not limited to sickle cell anemia.

As used herein, "antisense activity" means any detectable and/or measurable change attributable to the hybridization of an antisense compound to its target nucleic acid. In certain embodiments, antisense activity is a decrease in the amount or expression of a target nucleic acid compared to target nucleic acid levels in the absence of the antisense compound.

As used herein, "antisense compound" means a compound comprising an antisense oligonucleotide and optionally one or more additional features, such as a conjugate group or terminal group.

As used herein, "antisense oligonucleotide" means an oligonucleotide having a nucleobase sequence that is at least partially complementary to a target nucleic acid.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "cEt" or "constrained ethyl" means a ribosyl bicyclic sugar moiety wherein the second ring of the bicyclic sugar is formed via a bridge connecting the 4'-carbon and the 2'-carbon, wherein the bridge has the formula 4'-$CH(CH_3)$—O-2', and wherein the methyl group of the bridge is in the S configuration.

As used herein, "complementary" in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methyl cytosine ($^{m}$C) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "double-stranded" in reference to an antisense compound means an antisense compound comprising two oligomeric compounds that are complementary to each other and form a duplex, and wherein one of the two said oligomeric compounds comprises an antisense oligonucleotide.

As used herein, "effective erythropoiesis" means erythropoiesis that results in production of an amount of red blood cells within the standardized normal range, wherein the red blood cells are normal. As used herein, "ineffective erythropoiesis" means erythropoiesis that does not result in production of red blood cells or results in the production of an inadequate number of red blood cells and/or production of abnormal red blood cells. The determination of whether red blood cells are normal can be done using standard techniques that assess parameters of red blood cells, including but not limited to morphology.

As used herein, "EPO" means erythropoietin.

As used herein, "erythropoiesis stimulating agent" or "ESA" means an agent that stimulates endogenous erythropoiesis, production of red blood cells, or a combination thereof. Stimulation of endogenous erythropoiesis means an increase in the production of erythroid cells relative to the level before the stimulation. ESAs include, but are not limited to, recombinant erythropoietin, activin ligand traps (e.g., activin receptor type II (e.g., IIA or IIB) fusion proteins (e.g., the extracellular domain of the activin receptor type II and the Fc region of IgG); see, e.g., U.S. Pat. No. 8,173,601; WO 2016/183280), Luspatercept, Sotatercept, and cells engineered to produce EPO. In certain embodiments, the ESA promotes late-stage erythroid differentiation to red blood cells. In certain embodiments, the ESA inhibits activin receptor type IIB. In certain embodiments, the ESA comprises a peptide or protein that is capable of interacting with activin receptor type IIB. In certain embodiments, the ESA comprises a peptide or protein that is capable of binding activin receptor type IIB. In certain embodiments, the ESA comprises a peptide or protein that blocks activin receptor type IIB activity. In certain embodiments the peptide or protein is at least a portion of an antibody that binds to activin receptor type IIB. In certain embodiments, the ESA comprises Luspatercept. In certain embodiments, the ESA consists essentially of Luspatercept. In certain embodiments, the ESA consists of Luspatercept.

As used herein, "gapmer" means an antisense oligonucleotide comprising an internal "gap" region having a plurality of nucleosides that support RNase H cleavage positioned between external "wing" regions having one or more nucleosides, wherein the nucleosides comprising the internal gap region are chemically distinct from the terminal wing nucleosides of the external wing regions.

As used herein, "hepcidin up-regulator" means an agent that can promote production of endogenous hepcidin.

As used herein, "hepcidin agonist" means an agent that, when administered to a subject, has the same or a similar effect as hepcidin in the subject. In certain embodiments, hepcidin agonists are ferroportin inhibitors (e.g., WO 2017/068090).

As used herein, "hepcidin analog" means an hepcidin agonist that is structurally similar to hepcidin. In certain embodiments, hepcidin analogs are also hepcidin agonists.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "inhibit" or "inhibition" refers to a partial or complete reduction. For example, inhibiting a target nucleic acid means a partial or complete reduction of the amount and/or activity of the target nucleic acid. As used herein, "inhibitor" means a compound that inhibits the amount and/or activity of its designated target. As used herein, "ferroportin inhibitor" means a compound that inhibits the amount or activity of ferroportin. As used herein, "TMPRSS6 inhibitor" means a compound that inhibits the amount or activity of a TMPRSS6 nucleic acid and/or protein.

As used herein, the terms "internucleoside linkage" means a group or bond that forms a covalent linkage between adjacent nucleosides in an oligonucleotide. As used herein "modified internucleoside linkage" means any internucleoside linkage other than a naturally occurring, phosphate internucleoside linkage. Non-phosphate linkages are referred to herein as modified internucleoside linkages. "Phosphorothioate linkage" means a modified phosphate linkage in which one of the non-bridging oxygen atoms is replaced with a sulfur atom. A phosphorothioate internucleoside linkage is a modified internucleoside linkage. Modified internucleoside linkages include linkages that comprise abasic nucleosides.

As used herein, "iron absorption" means movement of iron from the intestinal tract into the bloodstream. Measurement of iron absorption is performed using standard techniques known to those of skill in the art of treating anemias.

As used herein, "iron disorder" is a disorder that adversely affects iron metabolism, iron regulation, and/or iron levels in the body. As used herein, "iron overload disorder" is an iron disorder in which the level of serum ferritin, serum iron, and/or iron in one or more organs is abnormally elevated.

As used herein, "iron restrictive agent" or "IRA" means an agent that reduces serum iron level and/or transferrin saturation by reducing or preventing iron absorption from the intestinal tract into the bloodstream and/or by reducing or preventing iron release from internal iron storage, such as from macrophages. Iron chelators are not IRAs. IRAs include, but are not limited to, TMPRSS6 inhibitors, hepcidin up-regulators, hepcidin agonists, and ferroportin inhibitors.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "linked nucleosides" are nucleosides that are connected in a continuous sequence (i.e. no additional nucleosides are present between those that are linked).

As used herein, "mismatch" or "non-complementary" means a nucleobase of a first oligonucleotide that is not complementary with the corresponding nucleobase of a second oligonucleotide or target nucleic acid when the first and second oligomeric compound are aligned.

As used herein, "mitigate" in reference to a method means improvement in at least one symptom and/or measurable outcome relative to the same symptom or measurable outcome in the absence of or prior to performing the method. In certain embodiments, mitigation is the reduction in the severity or frequency of a symptom or the delayed onset or slowing of progression in the severity or frequency of a symptom and/or disease.

As used herein, "MOE" means methoxyethyl. "2'-MOE" means a 2'-$OCH_2CH_2OCH_3$ group in place of the 2'-OH group of a ribosyl ring of a sugar moiety.

As used herein, "motif" means the pattern of unmodified and/or modified sugar moieties, nucleobases, and/or internucleoside linkages, in an oligonucleotide.

As used herein, "naturally occurring" means found in nature.

As used herein, "non-cyclic modified sugar" or "non-cyclic modified sugar moiety" means a modified sugar moiety that comprises a modification, such as a substituent, that does not form a bridge between two atoms of the sugar to form a second ring.

As used herein, "nucleobase" means a naturally occurring nucleobase or a modified nucleobase. As used herein an "unmodified nucleobase" is adenine (A), thymine (T), cytosine (C), uracil (U), and guanine (G). As used herein, a modified nucleobase is a group of atoms capable of pairing with at least one naturally occurring nucleobase. A universal base is a nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety.

As used herein, "oligomeric compound" means a compound consisting of an oligonucleotide and optionally one or more additional features, such as a conjugate group or terminal group.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water; sterile saline; or sterile buffer solution.

As used herein "pharmaceutically acceptable salts" means physiologically and pharmaceutically acceptable salts of compounds, such as oligomeric compounds, i.e., salts that retain the desired biological activity of the parent compound and do not impart undesired toxicological effects thereto.

As used herein "pharmaceutical composition" means a mixture of substances suitable for administering to a subject. For example, a pharmaceutical composition may comprise an antisense compound and a sterile aqueous solution.

As used herein, "phosphorus moiety" means a group of atoms comprising a phosphorus atom. In certain embodiments, a phosphorus moiety comprises a mono-, di-, or tri-phosphate, or phosphorothioate.

As used herein "prodrug" means a therapeutic agent in a form outside the body that is converted to a different form within the body or cells thereof. Typically conversion of a prodrug within the body is facilitated by the action of an enzymes (e.g., endogenous or viral enzyme) or chemicals present in cells or tissues and/or by physiologic conditions.

As used herein, "quality red blood cells" means red blood cells or progenitor erythroid cells that transport oxygen throughout the body as efficiently or nearly as efficiently as normal red blood cells and have longer lifespans than red blood cells in an anemia disease state that negatively impacts red blood cell lifespan (e.g., β-thalassemia, sickle cell disease, or MDS). Normal red blood cells and normal progenitor erythroid cells are examples of quality red blood cells.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded siRNA, and microRNA, including microRNA mimics. In certain embodiments, an RNAi compound modulates the amount, activity, and/or splicing of a target nucleic acid. The term RNAi compound excludes antisense oligonucleotides that act through RNase H.

As used herein, the term "single-stranded" in reference to an antisense compound and/or antisense oligonucleotide means such a compound consisting of one oligomeric compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex.

As used herein, "small molecule" means a molecule having a molecular weight equal to or less than 950 Daltons.

As used herein, "sugar moiety" means an unmodified sugar moiety or a modified sugar moiety. As used herein, "unmodified sugar moiety" means a 2'-OH(H) ribosyl moiety, as found in RNA (an "unmodified RNA sugar moiety"), or a 2'-H(H) moiety, as found in DNA (an "unmodified DNA sugar moiety"). As used herein, "modified sugar moiety" or "modified sugar" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include cyclic sugars, such as bicyclic sugars, and non-cyclic sugars. As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "target nucleic acid," "target RNA," "target transcript" and "nucleic acid target" mean a nucleic acid that an antisense compound affects via hybridization to the target.

As used herein, "terminal group" means a chemical group or group of atoms that is covalently linked to a terminus of an oligonucleotide.

Certain Embodiments

The present disclosure includes but is not limited to the following embodiments:

1. A method comprising administering an erythropoiesis stimulating agent (ESA) and an iron restrictive agent (IRA) to a subject having or at risk of having an anemia.
2. The method of embodiment 1, wherein the ESA comprises EPO producing cells.
3. The method of embodiment 1, wherein the ESA consists of EPO producing cells.
4. The method of embodiment 2 or 3, wherein the EPO producing cells are derived from cells obtained from the subject.
5. The method of any of embodiments 2-4, wherein the EPO producing cells are fibroblasts.
6. The method of any of embodiments 2-5, wherein the EPO producing cells are cells altered to produce EPO.
7. The method of embodiment 6, wherein the alteration comprises genetic engineering.
8. The method of embodiment 6 or 7, wherein the EPO producing cells produce higher levels of EPO than the levels of EPO produced by the cells from which the EPO producing cells were derived prior to the alteration.
9. The method of any of embodiments 2-8, wherein the EPO producing cells are administered to the subject by implantation into the subject.
10. The method of any of embodiments 2-9, wherein the EPO producing cells are $TARGT_{EPO}$ cells.
11. The method of embodiment 1 or 2, wherein the ESA comprises EPO.
12. The method of embodiment 1, wherein the ESA consists of EPO.
13. The method of embodiment 11 or 12, wherein the EPO is recombinant EPO.
14. The method of embodiment 11 or 12, wherein the EPO is exogenous EPO.
15. The method of embodiment 1, wherein the ESA comprises Luspatercept producing cells.
16. The method of embodiment 1, wherein the ESA consists of Luspatercept producing cells.
17. The method of embodiment 1, wherein the ESA comprises Sotatercept producing cells.
18. The method of embodiment 1, wherein the ESA consists of Sotatercept producing cells.
19. The method of embodiment 1 or 15, wherein the ESA comprises Luspatercept.
20. The method of embodiment 1, wherein the ESA consists of Luspatercept.
21. The method of embodiment 1 or 17, wherein the ESA comprises Sotatercept.
22. The method of embodiment 1, wherein the ESA consists of Sotatercept.
23. The method of embodiment 1, wherein the ESA is an agent that stimulates endogenous EPO production.
24. The method of any of embodiments 1-23, wherein the ESA is an agent that stimulates endogenous erythropoiesis.
25. The method of any of embodiments 1-24, wherein the IRA is a TMPRSS6 inhibitor.
26. The method of embodiment 25, wherein the TMPRSS6 inhibitor is an antisense compound, siRNA, or shRNA.
27. The method of embodiment 25 or 26, wherein the TMPRSS6 inhibitor comprises an antisense oligonucleotide having a nucleobase sequence that is at least 90% complementary to a TMPRSS6 transcript.
28. The method of embodiment 26 or 27, wherein the antisense compound is single-stranded.
29. The method of embodiment 27 or 28, wherein the nucleobase sequence of the antisense oligonucleotide is at least 95% complementary to a TMPRSS6 transcript.
30. The method of embodiment 27 or 28, wherein the nucleobase sequence of the antisense oligonucleotide is 100% complementary to a TMPRSS6 transcript.
31. The method of any of embodiments 27-30, wherein the TMPRSS6 transcript is a human transcript.
32. The method of any of embodiments 27-30, wherein the TMPRSS6 transcript is a human pre-mRNA.
33. The method of any of embodiments 27-30, wherein the TMPRSS6 transcript is a human mRNA.
34. The method of any of embodiments 27-33, wherein the antisense compound comprises the antisense oligonucleotide and a conjugate group.
35. The method of embodiment 34, wherein the conjugate group comprises at least one GalNAc moiety.
36. The method of embodiment 34 or 35, wherein the conjugate group comprises LICA-1.
37. The method of any of embodiments 34-36, wherein the conjugate group consists of LICA-1 and a phosphate linkage.

38. The method of any of embodiments 34-37, wherein the antisense compound consists of the antisense oligonucleotide and LICA-1, wherein the antisense oligonucleotide and the LICA-1 are linked by a phosphate linkage.
39. The method of any of embodiments 27-38, wherein the nucleobase sequence of the antisense oligonucleotide comprises or consists of SEQ ID NO: 3.
40. The method of any of embodiments 27-39, wherein the antisense oligonucleotide is a gapmer.
41. The method of any of embodiments 27-40, wherein the antisense oligonucleotide is a modified oligonucleotide.
42. The method of embodiment 41, wherein the antisense oligonucleotide comprises at least one modified sugar.
43. The method of embodiment 42, wherein the at least one modified sugar is a 2'-MOE modified sugar.
44. The method of any of embodiments 41-43, wherein the antisense oligonucleotide comprises at least one modified nucleobase.
45. The method of embodiment 44, wherein the at least one modified nucleobase is a 5-methylcytosine.
46. The method of any of embodiments 41-45, wherein the antisense oligonucleotide comprises at least one modified internucleoside linkage.
47. The method of embodiment 46, wherein the at least one modified internucleoside linkage is a phosphorothioate internucleoside linkage.
48. The method of embodiment 47, wherein each internucleoside linkage of the antisense oligonucleotide is independently selected from phosphate and phosphorothioate internucleoside linkages.
49. The method of embodiment 48, wherein the antisense oligonucleotide comprises at least one phosphate internucleoside linkage.
50. The method of embodiment 26 or 27, wherein the antisense compound is double-stranded.
51. The method of embodiment 50, wherein the antisense compound comprises an siRNA.
52. The method of any of embodiments 50-51, wherein at least one oligonucleotide of the antisense compound is a modified oligonucleotide.
53. The method of any of embodiments 50-52, wherein the antisense compound comprises a conjugate group.
54. The method of embodiment 53, wherein the conjugate group comprises at least one GalNAc moiety.
55. The method of any of embodiments 50-54, wherein the nucleobase sequence of one oligonucleotide of the antisense compound is at least 90% complementary to a human TMPRSS6 mRNA.
56. The method of embodiment 25, wherein the TMPRSS6 inhibitor is a small molecule.
57. The method of any of embodiments 1-24, wherein the IRA is an hepcidin up-regulator.
58. The method of embodiment 57, wherein the hepcidin up-regulator is an agent that promotes endogenous hepcidin production.
59. The method of any of embodiments 1-24, wherein the IRA is an hepcidin agonist.
60. The method of embodiment 59, wherein the hepcidin agonist is exogenous hepcidin.
61. The method of embodiment 59, wherein the hepcidin agonist is exogenous mini-hepcidin.
62. The method of embodiment 59, wherein the hepcidin agonist is an exogenous hepcidin analog.
63. The method of any of embodiments 1-24, wherein the IRA is a ferroportin inhibitor.
64. The method of embodiment 63, wherein the ferroportin inhibitor blocks the activity of ferroportin.
65. The method of any of embodiments 1-64, wherein the anemia is a thalassemia.
66. The method of embodiment 65, wherein the thalassemia is a beta-thalassemia.
67. The method of embodiment 66, wherein the beta-thalassemia is non-transfusion dependent.
68. The method of embodiment 66, wherein the beta-thalassemia is transfusion dependent.
69. The method of embodiment 65, wherein the thalassemia is an alpha-thalassemia.
70. The method of any of embodiments 65-68, wherein the thalassemia is combined with sickle cell anemia.
71. The method of any of embodiments 1-64, wherein the anemia is myelodysplastic syndrome.
72. The method of any of embodiments 1-64, wherein the anemia is not an iron overload disorder.
73. The method of any of embodiments 1-72, wherein the anemia is a hereditary anemia
74. The method of embodiment 73, wherein the hereditary anemia is sickle cell disease.
75. The method of any of embodiments 1-64, wherein the anemia is a severe chronic hemolytic anemia.
76. The method of embodiment 75, wherein the severe chronic hemolytic anemia is sickle cell disease.
77. The method of any of embodiments 1-76, wherein the subject has the anemia.
78. The method of any of embodiments 1-71 or 73-77, wherein the subject has the anemia with an iron overload disorder.
79. The method of any of embodiments 1-77, wherein the subject has the anemia without an iron overload disorder
80. The method of any of embodiments 1-79, wherein the subject is identified as having the anemia.
81. The method of any of embodiments 1-76, wherein the subject is at risk of having the anemia.
82. The method of any of embodiments 1-76, wherein the subject is identified as at risk of having the anemia.
83. The method of any of embodiments 1-82, wherein the ESA is administered parenterally to the subject.
84. The method of any of embodiments 1-82, wherein the ESA is administered subcutaneously to the subject.
85. The method of any of embodiments 1-82, wherein the ESA is administered orally to the subject.
86. The method of any of embodiments 1-85, wherein the IRA is administered parenterally to the subject.
87. The method of any of embodiments 1-85, wherein the IRA is administered subcutaneously to the subject.
88. The method of any of embodiments 1-85, wherein the IRA is administered orally to the subject.
89. The method of any of embodiments 1-88, wherein the ESA and IRA are administered on the same day.
90. The method of any of embodiments 1-89, wherein the ESA is administered before the IRA.
91. The method of any of embodiments 1-89, wherein the ESA is administered after the IRA.
92. The method of any of embodiments 1-88 or 90-91, wherein the ESA and IRA are administered on different days.
93. The method of any of embodiments 1-89, wherein the ESA and IRA are administered in the same formulation.
94. The method of any of embodiments 1-93, wherein at least one symptom of the anemia is mitigated in the subject.

95. The method of any of embodiments 1-94, wherein iron absorption is reduced in the subject.
96. The method of any of embodiments 1-95, wherein serum iron level is reduced in the subject.
97. The method of any of embodiments 1-96, wherein serum transferrin saturation level is reduced in the subject.
98. The method of any of embodiments 1-71, 73-78, or 80-97, wherein iron overload is reduced in the subject.
99. The method of any of embodiments 1-98, wherein effective erythropoiesis is increased in the subject.
100. The method of any of embodiments 1-99, wherein ineffective erythropoiesis is reduced in the subject.
101. The method of any of embodiments 1-100, wherein the level of total red blood cells is increased in the subject.
102. The method of any of embodiments 1-101, wherein the level of quality red blood cells is increased in the subject.
103. The method of any of embodiments 1-102, wherein morphology of red blood cells is improved in the subject.
104 The method of any of embodiments 1-103, wherein the lifespan of the red blood cells is increased in the subject.
105. The method of any of embodiments 1-104, wherein splenomegaly is reduced in the subject.
106. The method of any of embodiments 1-105, wherein extramedullary hematopoiesis is reduced in the subject.
107. The method of any of embodiments 1-106, wherein the level of hematocrit, hemoglobin, reticulocytes, MCH, and/or MCV is improved in the subject.
108. The method of any of embodiments 94-107, wherein the mitigation of the at least one symptom occurs in the subject following one or more administrations of the ESA and IRA and is relative to the severity or level of the same at least one symptom before the first administration of the ESA and IRA.
109 The method of any of embodiments 94-107, wherein the mitigation of the at least one symptom occurs in the subject following one or more administrations of the ESA and IRA and is relative to the severity or level of the same at least one symptom after administration of an ESA in the absence of an IRA.
110. The method of any of embodiments 94-107, wherein the mitigation of the at least one symptom occurs in the subject following one or more administrations of the ESA and IRA and is relative to the severity or level of the same at least one symptom after administration of an IRA in the absence of an ESA.
111. The method of any of embodiments 1-110, wherein the subject is a human subject.
112. The method of any of embodiments 93-111, wherein a pharmaceutical composition comprising the ESA and the IRA is administered to the subject.
113. The method of any of embodiments 89-92 or 94-111, wherein a first pharmaceutical composition comprising the ESA is administered to the subject and a second pharmaceutical composition comprising the IRA is administered to the subject.
114. Use of an ESA and an IRA for treatment of an anemia.
115. A composition comprising an ESA and an IRA.
116. The composition of embodiment 115, further comprising a pharmaceutically acceptable carrier.

I. Certain Methods of Administering an ESA and an IRA to a Subject for Treatment of Anemias The use of ESAs alone to treat certain types of anemias may improve the anemia by increasing the production of red blood cells. However, such stimulation of erythropoiesis can lead to worsening of certain symptoms, such as worsening of splenomegaly and suppression of hepcidin in anemias associated with iron overload. Moreover, the beneficial effect of erythroid-mediated consumption of stored iron may not be realized. In contrast, under conditions of reduced iron intake or absorption, the use of ESAs may correct both the iron overload and red blood cell production. For example, the results provided in Example 1 herein demonstrate that the combination of an ESA and an IRA remarkably improves many symptoms in a mouse model of β-thalassemia, including splenomegaly. Such benefits were not observed when ESAs were combined with different agents designed to improve iron overload, such as iron chelators. See, e.g., FIG. 1 herein and Casu et al. *Haematologica.* 101, e8-e11 (2016) and Casu et al. *Blood.* 128, 265-76 (2016).

In certain embodiments, the invention provides methods of administering an ESA and an IRA to a subject for the treatment of an anemia. In certain embodiments, the anemia is an iron overload disorder. In certain embodiments, the anemia is not an iron overload disorder. For instance, subjects having sickle cell disease patients do not show increased iron absorption nor spontaneous iron overload in the absence of chronic blood transfusion. In certain embodiments, sickling of red blood cells is reduced by a decrease in the amount of hemoglobin in each red blood cell due to administration of an IRA. In certain embodiments administration of an ESA and IRA to subjects having sickle cell disease increases the production of quality red blood cells. In certain embodiments, at least one symptom of the anemia is improved relative to treatment with one agent along and/or relative to treatment with neither an ESA nor an IRA.

II. Certain ESAs and IRAs

Certain ESAs have been described previously. In certain embodiments, ESAs are a direct source of EPO. In certain embodiments, ESAs stimulate the subject to produce more endogenous EPO. In certain embodiments, the ESA is a single compound or substance. In certain embodiments, the ESA is a composition comprising multiple compounds or substances. In certain embodiments, the ESA is a cellular composition. Examples of ESAs include, but are not limited to, recombinant EPO, activin ligand traps (e.g., activin receptor type II (e.g., IIA or IIB) fusion proteins (e.g., the extracellular domain of an activin receptor type II and an Fc region (e.g., from IgG1)) such as Luspatercept and Sotatercept, and cells engineered to produce EPO (e.g., $TARGT_{EPO}$ cells). Luspatercept and Sotatercept are described in Suragani et al. *Nat. Med.* 20, 408-14 (2014); Dussiot et al. *Nat. Med.* 20, 398-407 (2014); Platzbecker et al. *Lancet Oncol.* 18, 1338-47 (2017); Motta et al. *Expert Opin. Investig. Drugs* 26, 793-802 (2017), U.S. Pat. No. 8,173,601, and WO 2016/183280. In certain embodiments, the cells engineered to produce EPO are fibroblasts. In certain embodiments, the cells engineered to produce EPO are autologous. $TARGT_{EPO}$, or transduced autologous restorative gene therapy used for the production of EPO, is a method described in Shapir et. al. *Hum Gene Ther Clin Dev.* 26, 216-27 (2015) in which cells from a sample of a subject's dermis (from micro-organs from the abdominal dermis) are transduced ex vivo to carry an EPO gene.

Certain IRAs have been described previously. In certain embodiments, the IRA is a small molecule. In certain embodiments, the IRA is an antibody. In certain embodiments, the IRA is an antisense compound. Iron chelators are not IRAs, because they neither reduce or prevent iron absorption from the intestinal tract into the bloodstream nor reduce or prevent iron release from internal iron storage. Examples of IRAs include, but are not limited to, hepcidin, hepcidin up-regulators, hepcidin agonists, mini-hepcidin, hepcidin analogs, TMPRSS6 inhibitors, such as TMPRSS6 antisense compounds, and ferroportin inhibitors. Examples of TMPRSS6 inhibitors are described in WO 2016/161429 and WO 2012/135246.

III. Certain Oligonucleotides

In certain embodiments, the invention provides methods of administering agents that comprise or consist of compounds, e.g., antisense compounds and oligomeric compounds, that comprise or consist of oligonucleotides that consist of linked nucleosides. Oligonucleotides, such as antisense oligonucleotides, may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-cyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-cyclic modified furanosyl sugar moieties comprising one or more acyclic substituent, including but not limited to substituents at the 2', 4', and/or 5' positions. In certain embodiments, the furanosyl sugar moiety is a ribosyl sugar moiety. In certain embodiments one or more acyclic substituent of non-cyclic modified sugar moieties is branched. Examples of 2'-substituent groups suitable for non-cyclic modified sugar moieties include but are not limited to: 2'-F, 2'-$OCH_3$ ("OMe" or "O-methyl"), and 2'-$O(CH_2)_2OCH_3$ ("MOE"). In certain embodiments, 2'-substituent groups are selected from among: halo, allyl, amino, azido, SH, CN, OCN, $CF_3$, $OCF_3$, O—$C_1$-$C_{10}$ alkoxy, O—$C_1$-$C_{10}$ substituted alkoxy, O—$C_1$-$C_{10}$ alkyl, O—$C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—N($R_m$)($R_n$), where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for non-cyclic modified sugar moieties include but are not limited to alkoxy (e.g., methoxy), alkyl, and those described in Manoharan et al., WO 2015/106128. Examples of 5'-substituent groups suitable for non-cyclic modified sugar moieties include but are not limited to: 5'-methyl (R or S), 5'-vinyl, and 5'-methoxy. In certain embodiments, non-cyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted nucleoside or 2'-non-cyclic modified nucleoside comprises a sugar moiety comprising a non-bridging 2'-substituent group selected from: F, $NH_2$, $N_3$, $OCF_3$, $OCH_3$, $O(CH_2)_3NH_2$, $CH_2CH{=}CH_2$, $OCH_2CH{=}CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C(=O)$—N($R_m$)($R_n$)), where each $R_m$ and $R_n$ is, independently, H, an amino protecting group, or substituted or unsubstituted $C_1$-$C_{10}$ alkyl.

In certain embodiments, a 2'-substituted nucleoside or 2'-non-cyclic modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N$—$(CH_3)_2$, and $OCH_2C(=O)$—N(H)$CH_3$ ("NMA").

In certain embodiments, a 2'-substituted nucleoside or 2'-non-cyclic modified nucleoside comprises a sugar moiety comprising a non-bridging 2'-substituent group selected from: F. $OCH_3$, and $OCH_2CH_2OCH_3$.

Nucleosides comprising modified sugar moieties, such as non-cyclic modified sugar moieties, may be referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. In certain such embodiments, the furanose ring is a ribose ring. Examples of such 4' to 2' bridging sugar substituents include but are not limited to: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-CH($CH_3$)—O-2' (referred to as "constrained ethyl" or "cEt" when in the S configuration), 4'-$CH_2$—O—$CH_2$-2', 4'-$CH_2$—N(R)-2', 4'-CH($CH_2OCH_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C($CH_3$)($CH_3$)—O-2' and analogs thereof (see, e.g., Seth et al., U.S. Pat. No. 8,278,283), 4'-$CH_2$—N($OCH_3$)-2' and analogs thereof (see, e.g., Prakash et al., U.S. Pat. No. 8,278,425), 4'-$CH_2$—O—N($CH_3$)-2' (see, e.g., Allerson et al., U.S. Pat. No. 7,696,345 and Allerson et al., U.S. Pat. No. 8,124,745), 4'-$CH_2$—C(H)($CH_3$)-2' (see, e.g., Zhou, et al., *J. Org. Chem.,* 2009, 74, 118-134), 4'-$CH_2$—C(=$CH_2$)-2' and analogs thereof (see e.g., Seth et al., U.S. Pat. No. 8,278,426), 4'-C($R_aR_b$)—N(R)—O-2', 4'-C($R_aR_b$)—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

Additional bicyclic sugar moieties are known in the art, see, for example: Freier et al., *Nucleic Acids Research,* 1997, 25 (22), 4429-4443, Alback et al., *J. Org. Chem.,* 2006, 71, 7731-7740, Singh et al., *Chem. Commun.,* 1998, 4, 455-456; Koshkin et al., *Tetrahedron,* 1998, 54, 3607-3630; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 20017, 129, 8362-8379; Elayadi et al., Wengel et al., U.S. Pat. No. 7,053,207; Imanishi et al., U.S. Pat. No. 6,268,490; Imanishi et al. U.S. 6,770,748; Imanishi et al., U.S. RE44,779; Wengel et al., U.S. Pat. No. 6,794, 499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

F-HNA

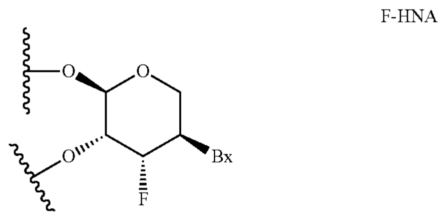

("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005, 906; F-HNA can also be referred to as a F-THP or 3'-fluoro tetrahydropyran).

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

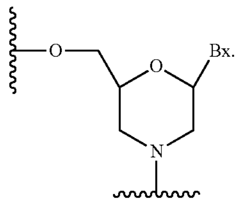

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.,* 2013, 11, 5853-5865), and nucleosides and oligonucleotides described in Manoharan et al., WO 2011/133876.

2. Certain Modified Nucleobases

In certain embodiments, oligonucleotides, e.g., antisense oligonucleotides, comprise one or more nucleoside comprising an unmodified nucleobase. In certain embodiments, modified oligonucleotides comprise one or more nucleoside comprising a modified nucleobase.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($-C{\equiv}C-CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15*, Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

B. Certain Modified Internucleoside Linkages

In certain embodiments, nucleosides of oligonucleotides, including antisense oligonucleotides, may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, and phosphorothioates ("P═S"), and phosphorodithioates ("HS—P═S"). Representative non-phosphorus containing internucleoside linking groups include but are not limited to methylenemethylimino (—$CH_2$—N($CH_3$)—O—$CH_2$—), thiodiester, thionocarbamate (—O—C(═O)(NH)—S—); siloxane (—O—$SiH_2$—O—); and N,N'-dimethylhydrazine (—$CH_2$—N($CH_3$)—N($CH_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-$CH_2$—N($CH_3$)—O-5'), amide-3 (3'-$CH_2$—C(═O)—N(H)-5'), amide-4 (3'-$CH_2$—N(H)—C(═O)-5'), formacetal (3'-O—$CH_2$—O-5'), methoxypropyl, and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

C. Certain Motifs

In certain embodiments, modified oligonucleotides, including modified antisense oligonucleotides, comprise one or more modified nucleoside comprising a modified sugar and/or a modified nucleobase. In certain embodiments, modified oligonucleotides, including modified antisense oligonucleotides, comprise one or more modified internucleoside linkage. In such embodiments, the modified, unmodified, and differently modified sugar moieties, nucleobases, and/or internucleoside linkages of a modified oligonucleotide, such as an antisense oligonucleotide, define a pattern or motif. In certain such embodiments, the patterns or motifs of sugar moieties, nucleobases, and internucleoside linkages are each independent of one another. Thus, a modified oligonucleotide, including an antisense oligonucleotide, may be described by its sugar motif, nucleobase motif and/or internucleoside linkage motif (as used herein, nucleobase motif describes the modifications to the nucleobases independent of the nucleobase sequence).

1. Certain Sugar Motifs

In certain embodiments, oligonucleotides, including antisense oligonucleotides, comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides, such as antisense oligonucleotides, comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least the sugar moieties of the terminal wing nucleosides of each of the wings differ from at least some of the sugar moieties of the nucleosides of the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxynucleoside.

The nucleosides on the gap side of each wing/gap junction are unmodified 2'-deoxyribosyl nucleosides and the nucleosides on the wing sides of each wing/gap junction are modified nucleosides. In certain such embodiments, each nucleoside of the gap is an unmodified 2'-deoxyribosyl nucleoside. In certain such embodiments, each nucleoside of each wing is a modified nucleoside.

2. Certain Nucleobase Motifs

In certain embodiments, oligonucleotides, including antisense oligonucleotides, comprise modified and/or unmodified nucleobases arranged along the oligonucleotide or region thereof in a defined pattern or motif. In certain embodiments, each cytosine is modified. In certain embodiments, some or all of the cytosine nucleobases are 5-methylcytosines.

3. Certain Internucleoside Linkage Motifs

In certain embodiments, oligonucleotides, including antisense oligonucleotides, comprise modified and/or unmodified internucleoside linkages arranged along the oligonucleotide or region thereof in a defined pattern or motif. In certain embodiments, essentially each internucleoside linking group is a phosphate internucleoside linkage (P═O). In certain embodiments, each internucleoside linking group of a modified oligonucleotide is a phosphorothioate (P═S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

D. Certain Lengths

In certain embodiments, oligonucleotides, including antisense oligonucleotides, can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

E. Certain Modified Oligonucleotides

In certain embodiments, the above modifications (sugar, nucleobase, internucleoside linkage) are incorporated into a modified oligonucleotide. In certain such embodiments, such modified oligonucleotides are antisense oligonucleotides. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists if of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

F. Nucleobase Sequence

In certain embodiments, oligonucleotides, such as antisense oligonucleotides, are further described by their nucleobase sequence. In certain embodiments, oligonucleotides have a nucleobase sequence that is complementary to a second oligonucleotide and/or a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 70%, at least 80%, at least 90%, at least 95%, or 100% complementary to the second oligonucleotide or nucleic acid, such as a target nucleic acid.

IV. Certain Oligomeric Compounds

In certain embodiments, the invention provides methods of administering agents that comprise or consist of compounds, such as antisense compounds, that comprise or consist of oligomeric compounds, which consist of an oligonucleotide (e.g., a modified, unmodified, and/or antisense oligonucleotide) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, abasic nucleosides, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, 277, 923-937), a tocopherol group (Nishina et al., *Molecular Therapy Nucleic Acids,* 2015, 4, e220; and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

In certain embodiments, a conjugate group comprises a cell-targeting conjugate moiety. In certain embodiments, a conjugate group has the general formula:

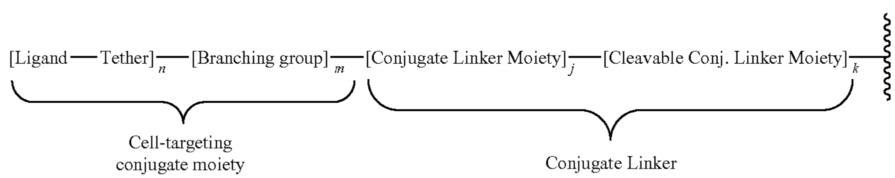

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, conjugate groups comprise a cell-targeting moiety having the formula:

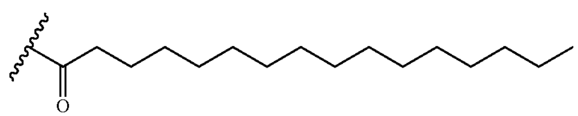 [SMILES: *C(=O)CCCCCCCCCCCCCCC]

In certain embodiments, conjugate groups comprise a cell-targeting moiety having the formula:

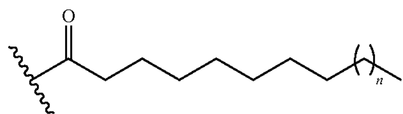

wherein n is an integer selected from 1, 2, 3, 4, 5, 6, or 7. In certain embodiments, n is 1. In certain embodiments, n is 2. In certain embodiments, n is 3. In certain embodiments, n is 4. In certain embodiments, n is 5.

In certain embodiments, conjugate groups comprise a cell-targeting moiety having the formula:

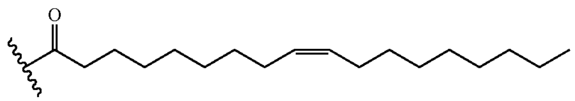 [SMILES: *C(=O)CCCCCCC/C=C\CCCCCCCC]

In certain embodiments, conjugate groups comprise a cell-targeting moiety having the formula:

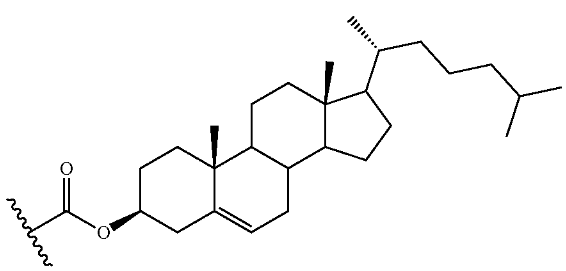

In certain embodiments, conjugate groups comprise a cell-targeting moiety having the formula:

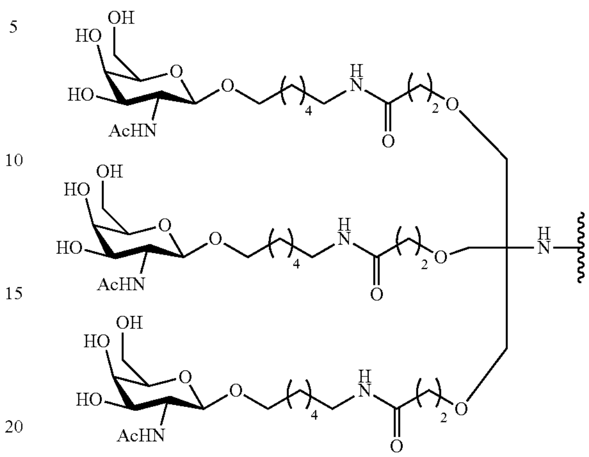

In certain embodiments, conjugate groups comprise a cell-targeting moiety having the formula:

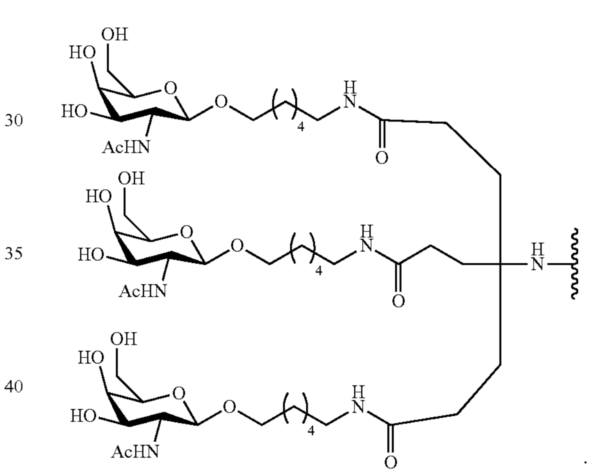

In certain embodiments, conjugate groups comprise a cell-targeting moiety having the formula:

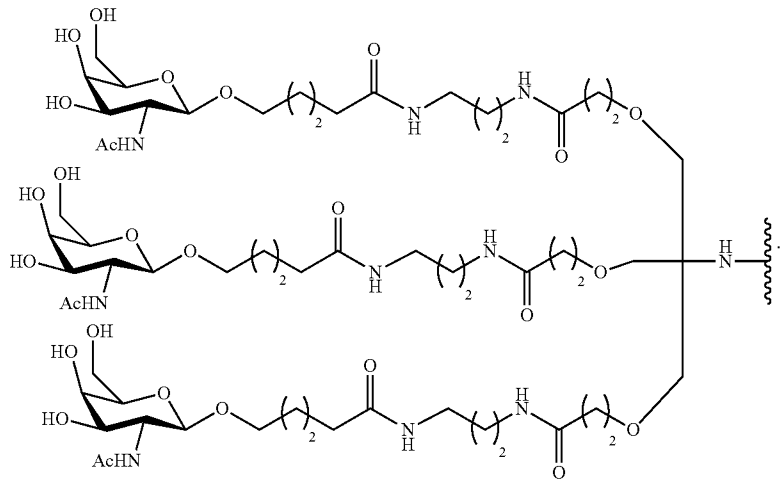

In certain embodiments, oligomeric compounds comprise a conjugate group described herein as "LICA-1". LICA-1 has the formula:

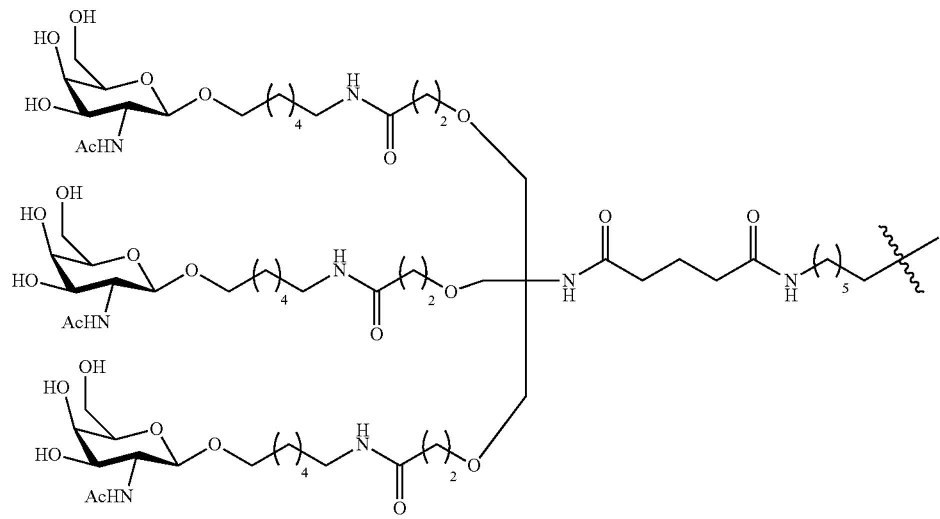

In certain embodiments, oligomeric compounds comprising LICA-1 have the formula:

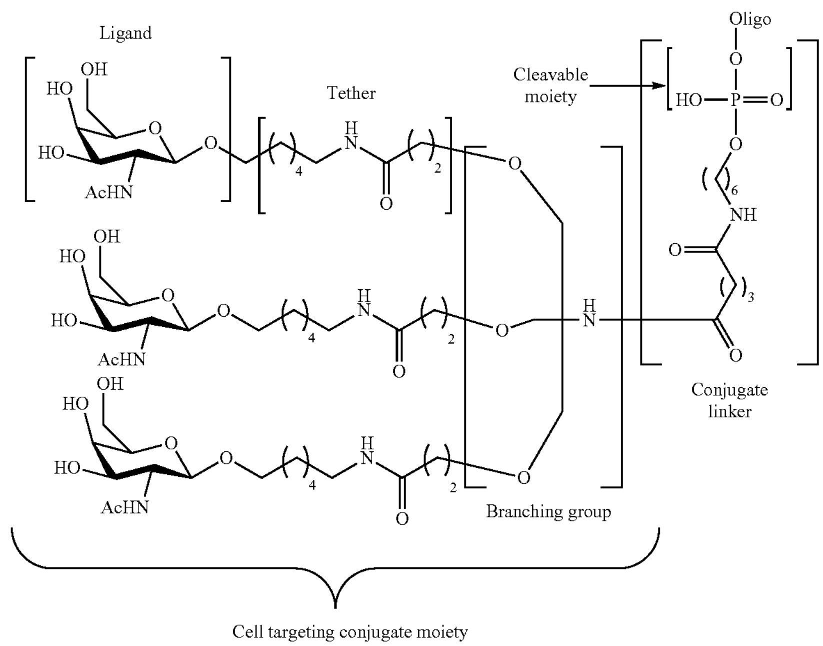

wherein oligo is an oligonucleotide.

2. Conjugate Linkers

Conjugate moieties are attached to oligonucleotides through conjugate linkers. In certain compounds comprising oligonucleotides, such as oligomeric compounds, the conjugate linker is a single chemical bond (i.e., the conjugate moiety is attached directly to an oligonucleotide through a single bond). In certain oligomeric compounds, a conjugate moiety is attached to an oligonucleotide via a more complex conjugate linker comprising one or more conjugate linker moieties, which are sub-units making up a conjugate linker.

In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, compounds of the invention are single-stranded. In certain embodiments, oligomeric compounds are paired with a second oligonucleotide or oligomeric compound to form a duplex, which is double-stranded.

V. Certain Antisense Compounds

In certain embodiments, the present invention provides agents that comprise or consist of an antisense compound, which comprises or consists of an oligomeric compound comprising an antisense oligonucleotide. In certain embodiments, antisense compounds are single-stranded. Such single-stranded antisense compounds typically comprise or consist of an oligomeric compound that comprises or consists of an antisense oligonucleotide and optionally a conjugate group. In certain embodiments, the antisense compound is complementary to a TMPRSS6 nucleic acid. In certain such embodiments, the antisense compound comprises CTTTATTCCAAAGGGCAGCT (SEQ ID NO: 3) or a sequence having at least 90% identity or 95% identity with SEQ ID NO: 3. In certain such embodiments, the antisense compound comprises a modified, antisense oligonucleotide having the nucleobase sequence CTTTATTCCAAAGGGCAGCT (SEQ ID NO: 3). In certain embodiments, the antisense compound comprises a LICA-1 conjugate group. In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of an antisense oligonucleotide and optionally a conjugate group. The oligonucleotide of the second oligomeric compound of such double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

In certain embodiments, oligomeric compounds of antisense compounds are capable of hybridizing to a target nucleic acid, resulting in at least one antisense activity. In certain embodiments, antisense compounds selectively affect one or more target nucleic acid. Such selective antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA: DNA duplex. The DNA in such an RNA: DNA duplex need not be unmodified DNA. In certain embodiments, the invention provides antisense compounds that are sufficiently "DNA-like" to elicit RNase H activity. Further, in certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain such embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain such embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, and/or a phenotypic change in a cell or animal. In certain such embodiments, the target nucleic acid is a target mRNA.

VI. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is a mRNA. In certain such embodiments, the target region is entirely within an exon. In certain embodiments, the target region spans an exon/exon junction. In certain embodiments, antisense compounds are at least partially complementary to more than one target nucleic acid. In certain embodiments, the target nucleic acid is a type-two transmembrane serine protease 6 (TMPRSS6) pre-mRNA. In certain embodiments, the target nucleic acid is a TMPRSS6 mRNA. In certain embodiments, the nucleobase sequence of the TMPRSS6 pre-mRNA comprises or consists of the complement of Genbank Number NC_000022.11, truncated from nucleotides 37062001 to 37113000 (SEQ ID NO: 1). In certain embodiments, the nucleobase sequence of the TMPRSS6 mRNA comprises or consists of Genbank Number NM_153609.3 (SEQ ID NO: 2).

A. Complementarity/Mismatches to the Target Nucleic Acid

In certain embodiments, antisense compounds comprise antisense oligonucleotides that are complementary to the target nucleic acid over the entire length of the oligonucleotide. In certain embodiments, such oligonucleotides are 99% complementary to the target nucleic acid. In certain embodiments, such oligonucleotides are 95% complementary to the target nucleic acid. In certain embodiments, such oligonucleotides are 90% complementary to the target nucleic acid. In certain embodiments, such oligonucleotides are 85% complementary to the target nucleic acid. In certain embodiments, such oligonucleotides are 80% complementary to the target nucleic acid. In certain embodiments, antisense oligonucleotides are at least 80% complementary to the target nucleic acid over the entire length of the oligonucleotide and comprise a region that is 100% or fully complementary to a target nucleic acid. In certain such embodiments, the region of full complementarity is from 6 to 20 nucleobases in length. In certain such embodiments, the region of full complementarity is from 10 to 18 nucleobases in length. In certain such embodiments, the region of full complementarity is from 18 to 20 nucleobases in length.

In certain embodiments, oligonucleotides comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the antisense compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region.

VII. Certain Pharmaceutical Compositions

In certain embodiments, the present invention provides pharmaceutical compositions comprising one or more agents. In certain embodiments, the one or more agents is an ESA and/or an IRA. In certain embodiments, the IRA is an antisense compound. In certain such embodiments, the pharmaceutical composition comprises at least one suitable pharmaceutically acceptable diluent or carrier. In certain embodiments, a pharmaceutical composition comprises a sterile saline solution and one or more agent. In certain embodiments, the sterile saline is pharmaceutical grade saline. In certain embodiments, a pharmaceutical composition comprises one or more agent and sterile water. In certain embodiments, the sterile water is pharmaceutical grade water. In certain embodiments, a pharmaceutical composition comprises one or more agent and phosphate-buffered saline (PBS). In certain embodiments, a pharmaceutical composition consists of one or more agent and sterile PBS. In certain embodiments, the sterile PBS is pharmaceutical grade PBS.

In certain embodiments, pharmaceutical compositions comprise one or more or antisense compound and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone. In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an antisense compound encompass any pharmaceutically acceptable salts of the antisense compound, esters of the antisense compound, or salts of such esters. In certain embodiments, pharmaceutical compositions comprising antisense compounds comprising one or more antisense oligonucleotide, upon administration to an animal, including a human, are capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an antisense compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

VIII. Certain Combinations and Combination Therapies

Methods provided herein comprise administering an ESA (first agent) and an IRA (second agent) to a subject. In certain embodiments, the second agent increases the activity of the first agent in the subject relative to the activity of the first agent in the subject in the absence of the second agent. In certain embodiments, co-administration of the first and second agents permits use of lower dosages than would be required to achieve a therapeutic or prophylactic effect if the agents were administered as independent therapies. In certain embodiments, administration of the first agent and the second agent result in therapeutic benefits that cannot be achieved using only one of the first or second agents alone.

In certain embodiments, the IRA is an antisense compound comprising or consisting of an antisense oligonucleotide and is co-administered with the ESA. In certain embodiments, the ESA and IRA are administered at different times. In certain embodiments, the ESA and IRA are prepared together in a single formulation. In certain embodiments, the ESA and IRA are prepared separately. In certain embodiments, the ESA and IRA are used in combination treatment by administering the ESA and IRA simultaneously, separately, or sequentially. In certain embodiments, they are formulated as a fixed dose combination product. In other embodiments, they are provided to the patient as separate units which can then either be taken simultaneously or serially (sequentially).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and other publications recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein have one or more asymmetric center and thus give rise to enantiomers, diastereomers, and other stereoisomeric configurations that may be defined, in terms of absolute stereochemistry, as (R) or(S), as α or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their racemic and optically pure forms. All tautomeric forms of the compounds provided herein are included unless otherwise indicated.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^{1}H$ hydrogen atoms. Isotopic substitutions encompassed by the compounds herein include but are not limited to: $^{2}H$ or $^{3}H$ in place of $^{1}H$, $^{13}C$ or $^{14}C$ in place of $^{12}C$, $^{15}N$ in place of $^{14}N$, $^{17}O$ or $^{18}O$ in place of $^{16}O$, and $^{33}S$, $^{34}S$, $^{35}S$, or $^{36}S$ in place of $^{32}S$. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

Example 1: Co-Administration of an Erythropoiesis Stimulating Agent and an Iron Restrictive Agent An erythropoiesis stimulating agent (ESA) and an iron restrictive agent (IRA) were co-administered to transgenic heterozygous $Hbb^{t3h/+}$ mice, a model system for β-thalassemia intermedia. The mouse model is described in Guo, et. al., *J. Clin. Invest.* 2013, 123 (4): 1531-1541. The ESA, TARGT (Transduced Autologous Restorative Gene Therapy), was used to deliver mouse erythropoietin (EPO) to $Hbb^{th3/+}$ mice. $TARGT_{EPO}$ comprises fibroblasts expressing EPO that were described in Shapir et. al. *Hum Gene Ther Clin Dev.* 26, 216-27 (2015). In brief, primal dermal fibroblasts were transfected with helper-dependent adenovirus expressing mouse EPO, embedded in Matrigel, and $1\times10^{6}$ cells were implanted in the dorsal area of the mice at age 2-5 months. The IRA was Compound No. 856416, a compound consisting of a modified antisense oligonucleotide 100% complementary to mouse Tmprss6 and a GalNAc conjugate group. The structure of Compound No. 856416 is LICA-$1_{o}G_{es}{}^{m}C_{eo}T_{eo}T_{eo}A_{eo}G_{ds}A_{ds}G_{ds}T_{ds}A_{ds}{}^{m}C_{ds}A_{ds}G_{ds}{}^{m}C_{ds}{}^{m}C_{ds}{}^{m}C_{eo}A_{eo}{}^{m}C_{es}T_{es}T_{e}$ (SEQ ID NO: 4), wherein LICA-1 is a conjugate group comprising three GalNAc sugars, subscript "e" represents a 2'-O-methoxyethyl (MOE) modified sugar, subscript "d" represents an unmodified 2'-deoxyribose, "$^{m}C$" represents a 5-methylcytosine, subscript "o" represents a phosphate internucleoside linkage, and subscript "s" represents a phosphorothioate internucleoside linkage.

The $Hbb^{th3/+}$ mice were divided into groups of 5-17 mice, some of which were treated with a low-iron diet, Compound No. 856416 or $TARGT_{EPO}$ or combination of these treatments, as indicated in Table 1. Respective p values for results presented in Table 1 are presented in Table 2. One group of 4 wild-type mice treated with only empty fibroblasts and one group of 11 $Hbb^{th3/+}$ mice treated with empty fibroblasts and a control oligonucleotide, Compound No. 856417, LICA-$1_{o}{}^{m}C_{es}{}^{m}C_{eo}T_{eo}T_{eo}{}^{m}C_{eo}{}^{m}C_{ds}{}^{m}C_{ds}T_{ds}G_{ds}A_{ds}A_{ds}G_{as}G_{as}T_{ds}T_{ds}{}^{m}C_{eo}{}^{m}C_{eo}T_{es}{}^{m}C_{es}{}^{m}C_{e}$ (SEQ ID NO: 5) were included as control groups. (Empty fibroblasts do not express EPO). Mice in low-iron diet groups were fed a low iron diet starting 6 weeks prior to sacrifice of the animals. The mice in groups treated with Compound No. 856416 received 5 mg/kg twice per week by intraperitoneal (IP) injection for 6 weeks prior to analysis, as for the $TARGT_{EPO}$ treatment. The mice in groups treated with $TARGT_{EPO}$ groups received the fibroblast implant as described above, 6 weeks before analysis, at which time mice were analyzed for changes in markers of β-thalassemia, including hemoglobin levels, spleen weight, and blood counts.

TABLE 1

| Mouse type | Treatment | Hb (g/dL) | RBC (x10$^{6}$ cells/μL) | HCT (%) | MCV (%) | MCH (%) | MCHC (g/dL) | Retic (x10$^{9}$ cells/L) | Spleen/BW |
|---|---|---|---|---|---|---|---|---|---|
| Wild type | Control (empty fibroblasts) | 14.7 ± 0.6 | 9.6 ± 0.4 | 48.5 ± 2.0 | 50.6 ± 0.1 | 15.3 ± 0.1 | 30.3 ± 0.3 | 440 ± 106 | 0.004 ± 0.000 |
| $Hbb^{th3/+}$ | Control (empty fibroblasts, scrambled ASO) | 7.7 ± 0.7 | 6.6 ± 0.7 | 28.8 ± 2.6 | 43.3 ± 2.0 | 11.5 ± 0.4 | 26.7 ± 0.9 | 2123 ± 434 | 0.020 ± 0.004 |
| $Hbb^{th3/+}$ | Low-iron diet | 7.4 ± 0.6 | 6.2 ± 0.5 | 27.5 ± 1.9 | 44.2 ± 2.0 | 11.8 ± 0.3 | 26.9 ± 1.7 | 2155 ± 315 | 0.024 ± 0.004 |
| $Hbb^{th3/+}$ | Compound No. 856416 | 9.0 ± 0.4 | 7.9 ± 0.3 | 27.7 ± 0.5 | 34.9 ± 1.0 | 11.3 ± 0.4 | 32.5 ± 1.0 | 655 ± 207 | 0.009 ± 0.003 |
| $Hbb^{th3/+}$ | $TARGT_{EPO}$ | 10.8 ± 1.3 | 9.1 ± 1.1 | 38.6 ± 4.6 | 42.7 ± 1.8 | 11.9 ± 0.2 | 28.0 ± 1.1 | 2457 ± 413 | 0.027 ± 0.005 |
| $Hbb^{th3/+}$ | Low-iron diet + $TARGT_{EPO}$ | 11.3 ± 1.5 | 9.6 ± 1.5 | 37.8 ± 5.4 | 39.7 ± 3.3 | 11.9 ± 0.5 | 29.9 ± 2.3 | 1639 ± 872 | 0.020 ± 0.007 |
| $Hbb^{th3/+}$ | Compound No. 856416 + $TARGT_{EPO}$ | 12.0 ± 1.0 | 10.0 ± 0.7 | 33.8 ± 2.3 | 33.9 ± 1.5 | 12.1 ± 1.0 | 35.7 ± 4.4 | 1033 ± 280 | 0.013 ± 0.003 |

TABLE 2

| P.Value | Control (empty fibroblasts, scrambled ASO) | Low-iron diet | Compound No. 856416 | $TARGT_{EPO}$ | Low-iron diet + $TARGT_{EPO}$ |
|---|---|---|---|---|---|
| Hemoglobin (g/dL): Compound No. 856416 + $TARGT_{EPO}$ | 0.0001 | 0.0001 | 0.0001 | NS | NS |
| Spleen/BW: Compound No. 856416 + $TARGT_{EPO}$ | 0.021 | 0.0001 | NS | 0.0001 | 0.0001 |

Ordinary One-Way ANOVA, Dunnett's Multiple Comparison Test

In wild-type animals, after three weeks, the combination of $TARGT_{EPO}$ with low iron diet significantly reduced Hb levels (−40%), RBC number (−38%) and reticulocytes (−80%), when compared to animals overexpressing Epo and receiving normal iron diet, indicating that the stored iron was insufficient to support the increased erythropoiesis.

In contrast, $Hbb^{th3/+}$ animals on iron deficient diet or—more particularly—treated with Tmprss6-ASO in the presence $TARGT_{EPO}$ showed improvement of anemia up to the end of the treatment. Strikingly, in these animals the improvement in the anemia was associated with reduced splenomegaly. Red blood cell numbers normalized and erythropoiesis in the bone marrow and spleen improved to normalization. Furthermore, organ iron concentration improved or normalized compared to control $Hbb^{th3/+}$ mice. In particular, in animals treated with Tmprss6-ASO and $TARGT_{EPO}$ the Hb levels increased significantly (on average 4.3 g/dL, reaching levels of 12 g/dl), and corresponding to 36% more that the baseline levels in $Hbb^{th3/+}$ control animals (7.7 g/dL) and +25% more compared to $Hbb^{th3/+}$ mice treated with Tmprss6-ASO alone (9.0 g/dL). The splenomegaly was reduced compared to baseline levels (−35%) and to animals treated only with TARGT-Epo (−52.4%).

These effects were not seen in $Hbb^{th3/+}$ animals treated with iron chelation (deferiprone (DFP)) and $TARGT_{EPO}$. These results are consistent with studies indicating that iron chelation does not improve erythropoiesis or splenomegaly (Casu et al. *Haematologica.* 101, e8-e11 (2016) and Casu et al. *Blood.* 128, 265-76 (2016)).

Hepcidin synthesis was increased significantly in $Hbb^{th3/+}$ mice treated with Tmprss6-ASO. Combining $TARGT_{EPO}$ administration with Tmprss6-ASO administration significantly increased levels of serum hepcidin protein beyond treatment with Tmprss6-ASO alone (P<0.01). Analysis was performed using One-way ANOVA with Sidak's multiple comparison adjustment. (n=6-14 per group). These results (mean±SD) are presented in Table 3.

TABLE 3

| Condition: | No treatment | Empty Fibroblasts | Tmprss6 ASO | Fibroblasts over-expressing EPO | Fibroblasts over-expressing EPO & Tmprss6 ASO |
|---|---|---|---|---|---|
| Serum Hamp (ng/ml) | 194.1 ± 0.9 | 232.0 ± 56.6 | 580.0 ± 66.7 | 165.8 ± 94.9 | 728.8 ± 75.3 |

Results presented in Example 1 demonstrate that administration of erythropoiesis stimulating agents and iron restrictive agents significantly improve anemia and decrease iron overload and splenomegaly in thalassemia.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A method for treating or inhibiting an anemia comprising administering an erythropoiesis stimulating agent (ESA) and an iron restrictive agent (IRA) to a subject having or at risk of having an anemia, wherein said IRA is a TMPRSS6 inhibitor, and wherein said TMPRSS6 inhibitor is an antisense compound, siRNA, or shRNA.

2. The method of claim 1, wherein the ESA comprises erythropoietin (EPO) producing cells.

3. The method of claim 2, wherein the EPO producing cells are derived from cells obtained from the subject.

4. The method of claim 2, wherein the EPO producing cells are fibroblasts.

5. The method of claim 2, wherein the EPO producing are derived from cells altered to produce EPO.

6. The method of claim 2, wherein administering comprises implanting the EPO producing cells into the subject.

7. The method of claim 2, wherein the EPO producing cells are $TARGT_{EPO}$ cells.

8. The method of claim 1, wherein the ESA comprises erythropoietin (EPO), Luspatercept producing cells, Sotatercept producing cells, Luspatercept, or Sotatercept.

9. The method of claim 1, wherein the ESA is capable of interacting with activin receptor IIB.

10. The method of claim 1, wherein the ESA is an agent that stimulates endogenous EPO production or endogenous erythropoiesis.

11. The method of claim 1, wherein the TMPRSS6 inhibitor is an antisense compound.

12. The method of claim 1, wherein the TMPRSS6 inhibitor comprises an antisense oligonucleotide having a nucleobase sequence that is at least 90% complementary to a TMPRSS6 transcript.

13. The method of claim 11, wherein the antisense compound is single-stranded, double-stranded, or a gapmer.

14. The method of claim 11, wherein the antisense compound comprises the antisense oligonucleotide and a conjugate group.

15. The method of claim 14, wherein the conjugate group comprises at least one GalNAc moiety or comprises LICA-1.

16. The method of claim 12, wherein the nucleobase sequence of the antisense oligonucleotide is SEQ ID NO: 3.

17. The method of claim 1, wherein the anemia is a thalassemia.

18. The method of claim 17, wherein the thalassemia is a beta-thalassemia.

19. The method of claim 18, wherein the beta-thalassemia is non-transfusion dependent.

20. The method of claim 18, wherein the beta-thalassemia is transfusion dependent.

21. The method of claim 17, wherein the thalassemia is an alpha-thalassemia.

22. The method of claim 1, wherein the ESA is administered parenterally, subcutaneously, or orally to the subject.

23. The method of claim 1, wherein the IRA is administered subcutaneously to the subject.

24. The method of claim 11, wherein the ESA comprises Luspatercept.

25. The method of claim 11, wherein the ESA comprises erythropoietin (EPO) producing cells.

26. The method of claim 11, wherein the ESA comprises erythropoietin (EPO).

* * * * *